US006962987B2

(12) United States Patent
Sim et al.

(10) Patent No.: US 6,962,987 B2
(45) Date of Patent: Nov. 8, 2005

(54) **BINDING DOMAINS FROM *PLASMODIUM VIVAX* AND *PLASMODIUM FALCIPARUM* ERYTHROCYTE BINDING PROTEINS**

(75) Inventors: Kim Lee Sim, Gaithersburg, MD (US); Chetan Chitnis, Washington, DC (US); Louis H. Miller, Bethesda, MD (US); David S. Peterson, Rockville, MD (US); Xin-Zhuan Su, Rockville, MD (US); Thomas E. Wellems, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/153,273

(22) Filed: May 21, 2002

(65) Prior Publication Data

US 2002/0169305 A1 Nov. 14, 2002

Related U.S. Application Data

(63) Continuation of application No. 09/210,288, filed on Dec. 11, 1998, now Pat. No. 6,392,026, which is a division of application No. 08/568,459, filed on Dec. 7, 1995, now Pat. No. 5,849,306, which is a continuation of application No. 08/119,677, filed on Sep. 10, 1993, now abandoned.

(51) Int. Cl.[7] ............................................. C07H 21/04
(52) U.S. Cl. ..................................................... 536/23.5
(58) Field of Search ........................................ 536/23.5

(56) References Cited

U.S. PATENT DOCUMENTS

| 5,144,007 | A | * | 9/1992 | Pfahl |
| 5,198,347 | A | | 3/1993 | Miller et al. |
| 5,849,306 | A | | 12/1998 | Sim |
| 5,993,827 | A | | 11/1999 | Sim |
| 6,392,026 | B1 | * | 5/2002 | Sim et al. |

FOREIGN PATENT DOCUMENTS

WO    WO 93/18160    9/1993

OTHER PUBLICATIONS

Adams, et al., A family of erythrocyte binding proteins of malaria parasites; Proc. Natl. Acad. Sci. USA, vol. 89, pp. 7085–7089; Aug. 1992.
Bamwell, J.W. , et al., In vitro Evaluation of the Role of the duffy Blood Group in Erythrocyte by *Plasmodium vivax* , J. Exp. Med., 169:1795–1802, May 1989.
Borst, et al., Antigenic Variation in Malaria, Cell 82:1–4, Jul. 14, 1995.

Chitnis, C., et al., Identification of the Erythrocyte Binding Domains . . . J. Exper. Med. 180:497–506, Aug., 1994.
Dalton, J.P., et al., Blocking the receptor–mediated invasion of erythrocytes by *Plasmodioum knolesi* malaria with sulfated polysaccharides and glycosaminoglyans, Eur. J. Biochem., 195:789–794, 1991.
Fang et al., Cloning of the *Plasmodium vivax* Duffy receptor; Mol and Biochem Parasitology; vol. 44(1), pp. 125–132; Jan. 1991.
Haynes, J.D., et al., Receptor–Like Specificity of a *Plasmodium knowlesi* Malarial Protein the Binds to Duffy Antigen Ligands on Erythrocytges, J. Expl. Med., 167:1873–1881, Jun. 1988.
Holt, E.H., et al., Erythrocyte Invasion by two *Plasmodium falciparum* Isolates Differing in Sialic Acid Dependency in the Presence of Glycophorin A Antibodies, Am. J. Trop. Med. Hyg., 40(3): 245–251, Mar. 1989.
Miller, L. H., et al., Identification of *Plasmodium knowlesi* erythrocyte binding proteins, Molecular and Biochemical Parasitology, 31:217–222, 1988.
Orlandi, P.A., et al., Characterization of the 175–kilodalton erythrocyte binding antigen of *Plasmodium falciparum*, Molecular and Biochemical Parasitology, 40:285–294, 1990.
Perkins, M.E., et al., Sialic Acid–Dependent Binding of *Plasmodium falciparum* Merozoite Surface Antigen, Pf200, to Human Erythrocytes, J. of Immunology, 141(9):3190–3196, Nov. 1, 1998.
Sim et al., Primary structure of the 175K *Plasmodium falciparum* Erythrocyte binding antigen and identification of a peptide which elicits antibodies that inhibit malaria merozoite invasion; J of Cell Biology, vol. 111, pp. 1877–1884; Nov., 1990.
Sim, et al., Receptor ad Ligand Domains for Invasion of Erythrocytes by *Plasmodium falciparum*, Science 264:1941–1944, Jun. 24, 1994.
Su, et al., the Large Diverse gene Family var Encodes Proteins Involved in Cytoadherence and Antigenic . . . Cell 82:89–100, Jul. 14, 1985.
Wertheimer, S.P., et al., *Plasmodium vivzx* Interaction with the Human Duffy Blood Group glycoprotein: Indentification of a Parasite Receptor–like Protein, Experimental Parasitology, 69:340–350, 1989.

* cited by examiner

*Primary Examiner*—Mark Navarro
(74) *Attorney, Agent, or Firm*—Knobbe, Martens, Olson & Bear, LLP

(57) ABSTRACT

The present invention provides isolated polypeptides useful in the treatment and prevention of malaria caused by *Plasmodium falciparum* or *P. vivax*. In particular, the polypeptides are derived from the binding domains of the proteins in the EBL family as well as the sialic acid binding protein (SABP) on *P. falciparum* merozoites. The polypeptides may also be derived from the Duffy antigen binding protein (DABP) on *P. vivax* merozoites.

1 Claim, 7 Drawing Sheets

Family 1

| | | | |
|---|---|---|---|
| DABP | $C-X_{12}-C-X_5$ | --VCIPDRRYQLCMKEL-$X_{47}$- | DFCKDIRWSLGDFGDIIMGTDMEGIGYSK-$X_{11}$- |
| SABP F1 | $C-X_{10}-C-X_9$ | --VCIPDRRIQLCIVNL-$X_{36}$- | KFCNDLKNSFLDYGHLAMGNDMDFGGYST-$X_{17}$- |
| SABP F2 | $C-X_{13}-C-X_{10}$ | -VCVPPRRQELCLGNI-$X_{36}$- | EVCKIINKTFADIRDIIGGTDYWNDLSNR-$X_{15}$- |
| EBL-e1 | $C-X_{12}-C-X_{11}$ | -VCGPPRRQQLCLGYI-$X_{36}$- | KICNAILGSYADIGDIVRGLDVWRDINTN-$X_{17}$- |

Family 2

| | | | |
|---|---|---|---|
| EBL-e2 | ---------- | ----ACAPYRRLHLCDYNL-$X_{43}$- | QLCTVLARSFADIGDIVRGKDLYLGYDNK-$X_{37}$- |
| Proj3 F1 | $C-X_{15}-C-X_{15}$ | -ACAPYRRLHVCDQNL-$X_{45}$- | QICTMLARSFADIGDIVRGRDLYLGNPQE-$X_{30}$- |
| Proj3 F2 | $C-X_{17}-C-X_{31}$ | -VFLPPRREHMCTSNL-$X_{55}$- | AMCRAVRYSFADLGDIIRGRDMWDEDKSS-$X_{32}$- |
| Proj3 F3 | $C-X_{10}-C-X_{10}$ | -ACMPPRRQKLCLYYI-$X_{52}$- | QFLRSMYTEGDYRDICLNTDISKKQNDV-$X_{15}$- |
| E31a | $C-X_{10}-C-X_{11}$ | -ACIPPRRQKLCLHYL-$X_{51}$- | DFKRQMFYTFADYRDICLGTDISSKKDTS-$X_{15}$- |

Family 1   Cont'd

| | | |
|---|---|---|
| DABP | TDEKAQQRRKQWNESKAQIWTAMMYSV-$X_{11}$-C-$X_8$ | --ePQIYRWIREWGRDYVSELPTEVQKLKEKC--$X_{11}$ | --C-$X_1$-- |
| SABP F1 | SEHKIKNFRKEWWNEFREKLWEAMLSEH-$X_5$ | --C-$X_6$--eLQITQWIKEWHGEFLLERDNRSKLPKSKC--$X_8$ | --C-$X_0$-- |
| SABP F2 | NKKNDKLFRDEWWKVIKKDVWNVISWVF-$X_5$ | --C-$X_7$--IPQFFRWFSEWGDDYCQDKTKMIETLLVEC--$X_4$ | --C-$X_1$-- |
| EBL-e1 | KKQNDNNERNKWWEKQRNLIWSSMVKHI-$X_5$ | --C-$X_8$--IPQFLRWLKEWGDEFCEEMGTEVKQLEKIC--$X_4$ | --C-$X_1$-- |

FIG. 1B

Family 2 Cont'd

```
EBL-e2    KGGDFFQLREDWTSNRETVWKALICHA-X₁₁-C-X₂₃-VPQYLRWFEEWAEDFCRKKKKLENLQKQC-X₆---C-X₁₅--
Proj3 F1  NDPEFFKLREDWTANRETVWKAITCNA-X₉-C-X₂₃-VPQYLRWFEEWAEDFCRKKNKKIKDVKRNC-X₁₂---C-X₂₂--
Proj3 F2  KKPAYKKLRADWWEANRHQVWRAMKCAT-X₄-C-X₈-IPQRLRWMTEWAEWYCKAQSQEYDKLKKIC-X₁₁---C-X₆--
Proj3 F3  SKSPSGLSRQEWWKTNGPEIWKGMLCAL-X₃₇-KPQFLRWMIEWGEEFCAERQKKENIIKDAC-X₈---C-X₃--
E31a      KISNSIRYRKSWWETNGPVIWEGMLCAL-X₄₂-RPQFLRWLTEWGENFCKEQKKEYKVLLAKC-X₁₁---C-X₃--
```

Family 1 Cont'd

```
DABP     VPPCQNACKSYDQ   WITRKKN-X₅₆-------------CX---C    (SEQ ID NO:13)
SABP F1  EKECIDPCMKYRD   WIIRSKF-X₄₁-C-X₇--------CX---C    (SEQ ID NO:14)
SABP F2  DDNCKSKCNSYKE   WISKKKK-X₃₆-C-X₂₀-------CXX-C    (SEQ ID NO:15)
EBL-e1   EKKCKNACSSYEK   WIKERKN-X₃₈-C-X₁₉-------CXX-C    (SEQ ID NO:16)
```

Family 2 Cont'd

```
EBL-e2    CTNCSVWCRMYET             WIDNQKK-X₆₈-C-X₃₀-------CXX-C    (SEQ ID NO:18)
Proj3 F1  CISCLYACNPYVD             WIDNQKK-X₆₉-C-X₄₀-------CXX-C    (SEQ ID NO:19)
Proj3 F2  CGKCKAACDKYKEEIEKWNEQWRK-X₇₃-C-X₆-C-X₃₀-CXX-C                (SEQ ID NO:20)
Proj3 F3  KHRCNQACRAYQE             YVENKKK-X₄₃-C-X₄--------CX---C    (SEQ ID NO:21)
E31a      CVACKDQCKQYHS             WIGIWID-X₄₂-C-X₈--------CXXXC    (SEQ ID NO:17)
```

FIG. 3A

Concensus amino acid sequences and the synthetic oligonucleotide primers designed from them.

I. UNIEBP5 and 5A: PRRQK/ELC (SEQ ID NO: 22)

UNIEBP5, for A+T biased condon usage:
CC(A/G)-AG(G/A)-AG(G/A)-CAA-(G/A)AA-(C/T)TA-TG (SEQ ID NO: 23)

UNIEBP5A, for G+C biased codon usage:
CC(C/G)-(C/A)G(C/G)-(C/A)G(C/G)-CAG-CAG-(C/T)T(C/G)-TG (SEQ ID NO: 24)

II. UNIEBP5 B and C: FADI/YG/RDI (SEQ ID NO: 25)

UNIEBP5B, for A+T biased codon usage:
TTT-GC(A/T)-GAT-(A/T)(A/T)-(G/C)G(A/T)-GAT-AT (SEQ ID NO: 26)

UNIEBP5C, for G+C biased codon usage:
TTC-GC(G/C)-GAT-(A/T)(A/T)C-(G/C)G(G/C)-GAC-AT (SEQ ID NO: 27)

FIG. 3B

III. UNIEBP3 and 3A:   PQFL/FRW

UNIEBP3, for A+T biased codon usage:
CCA-(A/T)C(T/G)-(T/G)A(A/G)-(A/G)AA-TTG-(A/T)GG    (SEQ ID NO: 28)

UNIEBP3A, for G+C biased codon usage:
CCA-(C/G)C(G/T)-G(A/T)A-GA(A/T)-CTG-(C/G)GG    (SEQ ID NO: 29)

IV. UNIEBP3 and C:   EWGD/ED/EY/FC

UNIEBP3B, for A+T biased codon usage:
CA-A(A/T)A-(A/T)TC-(A/T)TC-(A/T)CC-CCA-TTC    (SEQ ID NO: 30)

UNIEBP3C, for G+C biased codon usage:
CA-G(A/T)A-(G/C)TC-(G/C)TC-(G/C)CC-CCA-CTC    (SEQ ID NO: 31)

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 4084 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Plasmodium vivax (xi) SEQUENCE DESCRIPTION: SEQ ID NO: 1:

```
AAGCTTTTAA AAATAGCAAC AAAATTTCGA AACATTGCCA CAAAAATTTT ATGTTTTACA      60

TATATTTAGA TTCATACAAT TTAGGTGTAC CCTGTTTTTT GATATATGCG CTTAAATTTT     120

TTTTTCGCTC ATATGTTTAG TTATATGTGT AGAACAACTT GCTGAATAAA TTACGTACAC     180

TTTCTGTTCT GAATAATATT ACCACATACA TTTAATTTTA AATACTATGA AAGGAAAAAA     240

CCGCTCTTTA TTTGTTCTCC TAGTTTTATT ATTGTTACAC AAGGTATCAT ATAAGGATGA     300

TTTTTCTATC ACACTAATAA ATTATCATGA AGGAAAAAAA TATTTAATTA TACTAAAAAG     360

AAAATTAGAA AAAGCTAATA ATCGTGATGT TTGCAATTTT TTTCTTCATT TCTCTCAGGT     420

AAATAATGTA TTATTAGAAC GAACAATTGA AACCCTTCTA GAATGCAAAA ATGAATATGT     480

GAAAGGTGAA AATGGTTATA AATTAGCTAA AGGACACCAC TGTGTTGAGG AAGATAACTT     540

AGAACGATGG TTACAAGGAA CCAATGAAAG AAGAAGTGAG GAAAATATAA AATATAAATA     600

TGGAGTAACG GAACTAAAAA TAAAGTATGC GCAAATGAAT GGAAAAAGAA GCAGCCGCAT     660

TTTGAAGGAA TCAATTTACG GGGCGCATAA CTTTGGAGGC AACAGTTACA TGGAGGGAAA     720

AGATGGAGGA GATAAAACTG GGGAGGAAAA AGATGGAGAA CATAAAACTG ATAGTAAAAC     780

TGATAACGGG AAAGGTGCAA ACAATTTGGT AATGTTAGAT TATGAGACAT CTAGCAATGG     840

CCAGCCAGCG GGAACCCTTG ATAATGTTCT TGAATTTGTG ACTGGGCATG AGGGAAATTC     900

TCGTAAAAAT TCCTCGAATG GTGGCAATCC TTACGATATT GATCATAAGA AAACGATCTC     960

TAGTGCTATT ATAAATCATG CTTTTCTTCA AAATACTGTA ATGAAAAACT GTAATTATAA    1020
```

```
GAGAAAACGT CGGGAAAGAG ATTGGGACTG TAACACTAAG AAGGATGTTT GTATACCAGA    1080

TCGAAGATAT CAATTATGTA TGAAGGAACT TACGAATTTG GTAAATAATA CAGACACAAA    1140

TTTTCATAGG GATATAACAT TTCGAAAATT ATATTTGAAA AGGAAACTTA TTTATGATGC    1200

TGCAGTAGAG GGCGATTTAT TACTTAAGTT GAATAACTAC AGATATAACA AAGACTTTTG    1260

CAAGGATATA AGATGGAGTT TGGGAGATTT TGGAGATATA ATTATGGGAA CGGATATGGA    1320

AGGCATCGGA TATTCCAAAG TAGTGGAAAA TAATTTGCGC AGCATCTTTG GAACTGATGA    1380

AAAGGCCCAA CAGCGTCGTA AACAGTGGTG GAATGAATCT AAAGCACAAA TTTGGACAGC    1440

AATGATGTAC TCAGTTAAAA AAAGATTAAA GGGGAATTTT ATATGGATTT GTAAATTAAA    1500

TGTTGCGGTA AATATAGAAC CGCAGATATA TAGATGGATT CGAGAATGGG AAGGGATTA    1560

CGTGTCAGAA TTGCCCACAG AAGTGCAAAA ACTGAAAGAA AAATGTGATG GAAAAATCAA    1620

TTATACTGAT AAAAAAGTAT GTAAGGTACC ACCATGTCAA AATGCGTGTA ATCATATGA    1680

TCAATGGATA ACCAGAAAAA AAAATCAATG GGATGTTCTG TCAAATAAAT TCATAAGTGT    1740

AAAAAACGCA GAAAAGGTTC AGACGGCAGG TATCGTAACT CCTTATGATA TACTAAAACA    1800

GGAGTTAGAT GAATTTAACG AGGTGGCTTT TGAGAATGAA ATTAACAAAC GTGATGGTGC    1860

ATATATTGAG TTATGCGTTT GTTCCGTTGA AGAGGCTAAA AAAAATACTC AGGAAGTTGT    1920

GACAAATGTG GACAATGCTG CTAAATCTCA GGCCACCAAT TCAAATCCGA TAAGTCAGCC    1980

TGTAGATAGT AGTAAAGCGG AGAAGGTTCC AGGAGATTCT ACGCATGGAA ATGTTAACAG    2040

TGGCCAAGAT AGTTCTACCA CAGGTAAAGC TGTTACGGGG GATGGTCAAA ATGGAAATCA    2100

GACACCTGCA GAAAGCGATG TACAGCGAAG TGATATTGCC GAAAGTGTAA GTGCTAAAAA    2160

TGTTGATCCG CAGAAATCTG TAAGTAAAAG AAGTGACGAC ACTGCAAGCG TTACAGGTAT    2220

TGCCGAAGCT GGAAAGGAAA ACTTAGGCGC ATCAAATAGT CGACCTTCTG AGTCCACCGT    2280

TGAAGCAAAT AGCCCAGGTG ATGATACTGT GAACAGTGCA TCTATACCTG TAGTGAGTGG    2340

TGAAAACCCA TTGGTAACCC CCTATAATGG TTTGAGGCAT TCGAAAGACA ATAGTGATAG    2400

CGATGGACCT GCGGAATCAA TGGCGAATCC TGATTCAAAT AGTAAAGGTG AGACGGGAAA    2460

GGGGCAAGAT AATGATATGG CGAAGGCTAC TAAAGATAGT AGTAATAGTT CAGATGGTAC    2520

CAGCTCTGCT ACGGGTGATA CTACTGATGC AGTTGATAGG GAAATTAATA AAGGTGTTCC    2580

TGAGGATAGG GATAAAACTG TAGGAAGTAA AGATGGAGGG GGGGAAGATA ACTCTGCAAA    2640

TAAGGATGCA GCGACTGTAG TTGGTGAGGA TAGAATTCGT GAGAACAGCG CTGGTGGTAG    2700

CACTAATGAT AGATCAAAAA ATGACACGGA AAAGAACGGG GCCTCTACCC CTGACAGTAA    2760

ACAAAGTGAG GATGCAACTG CGCTAAGTAA AACCGAAAGT TTAGAATCAA CAGAAAGTGG    2820

AGATAGAACT ACTAATGATA CAACTAACAG TTTAGAAAAT AAAAATGGAG AAAAGAAAA    2880

GGATTTACAA AAGCATGATT TTAAAAGTAA TGATACGCCG AATGAAGAAC CAAATTCTGA    2940

TCAAACTACA GATGCAGAAG GACATGACAG GGATAGCATC AAAAATGATA AGCAGAAAG    3000

GAGAAAGCAT ATGAATAAAG ATACTTTTAC GAAAAATACA AATAGTCACC ATTTAAATAG    3060

TAATAATAAT TTGAGTAATG GAAAATTAGA TATAAAAGAA TACAAATACA GAGATGTCAA    3120

AGCAACAAGG GAAGATATTA TATTAATGTC TTCAGTACGC AAGTGCAACA ATAATATTTC    3180

TTTAGAGTAC TGTAACTCTG TAGAGGACAA AATATCATCG AATACTTGTT CTAGAGAGAA    3240

AAGTAAAAAT TTATGTTGCT CAATATCGGA TTTTTGTTTG AACTATTTTG ACGTGTATTC    3300

TTATGAGTAT CTTAGCTGCA TGAAAAAGGA ATTTGAAGAT CCATCCTACA AGTGCTTTAC    3360
```

-continued

```
GAAAGGGGGC TTTAAAGGTA TGCAGAAAAA GATGCTGAAT AGAGAAAGGT GTTGAGTAAA    3420

TTAAAAAGGA ATTAATTTTA GGAATGTTAT AAACATTTTT GTACCCAAAA TTCTTTTTGC    3480

AGACAAGACT TACTTTGCCG CGGCGGGAGC GTTGCTGATA CTGCTGTTGT TAATTGCTTC    3540

AAGGAAGATG ATCAAAAATG AGTAACCAGA AAATAAAATA AAATAACATA AAATAAAATA    3600

AAAACTAGAA TAACAATTAA AATAAAATAA AATGAGAAAT GCCTGTTAAT GCACAGTTAA    3660

TTCTAACGAT TCCATTTGTG AAGTTTTAAA GAGAGCACAA ATGCATAGTC ATTATGTCCA    3720

TGCATATATA CACATATATG TACGTATATA TAATAAACGC ACACTTTCTT GTTCGTACAG    3780

TTCTGAAGAA GCTACATTTA ATGAGTTTGA AGAATACTGT GATAATATTC ACAGAATCCC    3840

TCTGATGCCT AACAGTAATT CAAATTTCAA GAGCAAAATT CCATTTAAAA AGAAATGTTA    3900

CATCATTTTG CGTTTTTCTT TTTTTCTTTT TTTTTTCTTT TTTAGATATT GAACACATGC    3960

AGCCATCAAC CCCCCTGGAT TATTCATGAT GCTACTTTGG TAAGTAAAAG CAATTCTGAT    4020

TGTAGTGCTG ATGTAATTTT AGTCATTTTG CTTGCTGCAA TAAACGAGAA AATATATCAA    4080

GCTT                                                                4084
```

(2) INFORMATION FOR SEQ ID NO: 2:

(i) SEQUENCE CHARACTERISTICS:
        (A) LENGTH: 1115 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium vivax (xi) SEQUENCE DESCRIPTION: SEQ ID NO: 2:

```
Met Lys Gly Lys Asn Arg Ser Leu Phe Val Leu Val Leu Leu Leu
 1               5                  10                  15

Leu His Lys Val Ser Tyr Lys Asp Asp Phe Ser Ile Thr Leu Ile Asn
            20                  25                  30

Tyr His Glu Gly Lys Lys Tyr Leu Ile Ile Leu Lys Arg Lys Leu Glu
        35                  40                  45

Lys Ala Asn Asn Arg Asp Val Cys Asn Phe Phe Leu His Phe Ser Gln
    50                  55                  60

Val Asn Asn Val Leu Leu Glu Arg Thr Ile Glu Thr Leu Leu Glu Cys
65                  70                  75                  80

Lys Asn Glu Tyr Val Lys Gly Glu Asn Gly Tyr Lys Leu Ala Lys Gly
                85                  90                  95

His His Cys Val Glu Glu Asp Asn Leu Glu Arg Trp Leu Gln Gly Thr
            100                 105                 110

Asn Glu Arg Arg Ser Glu Glu Asn Ile Lys Tyr Lys Tyr Gly Val Thr
        115                 120                 125

Glu Leu Lys Ile Lys Tyr Ala Gln Met Asn Gly Lys Arg Ser Ser Arg
    130                 135                 140

Ile Leu Lys Glu Ser Ile Tyr Gly Ala His Asn Phe Gly Gly Asn Ser
145                 150                 155                 160

Tyr Met Glu Gly Lys Asp Gly Gly Asp Lys Thr Gly Glu Glu Lys Asp
                165                 170                 175

Gly Glu His Lys Thr Asp Ser Lys Thr Asp Asn Gly Lys Gly Ala Asn
            180                 185                 190
```

-continued

```
Asn Leu Val Met Leu Asp Tyr Glu Thr Ser Ser Asn Gly Gln Pro Ala
        195                 200                 205
Gly Thr Leu Asp Asn Val Leu Glu Phe Val Thr Gly His Glu Gly Asn
    210                 215                 220
Ser Arg Lys Asn Ser Ser Asn Gly Gly Asn Pro Tyr Asp Ile Asp His
225                 230                 235                 240
Lys Lys Thr Ile Ser Ser Ala Ile Ile Asn His Ala Phe Leu Gln Asn
                245                 250                 255
Thr Val Met Lys Asn Cys Asn Tyr Lys Arg Lys Arg Glu Arg Asp
            260                 265                 270
Trp Asp Cys Asn Thr Lys Lys Asp Val Cys Ile Pro Asp Arg Arg Tyr
        275                 280                 285
Gln Leu Cys Met Lys Glu Leu Thr Asn Leu Val Asn Asn Thr Asp Thr
    290                 295                 300
Asn Phe His Arg Asp Ile Thr Phe Arg Lys Leu Tyr Leu Lys Arg Lys
305                 310                 315                 320
Leu Ile Tyr Asp Ala Ala Val Glu Gly Asp Leu Leu Leu Lys Leu Asn
                325                 330                 335
Asn Tyr Arg Tyr Asn Lys Asp Phe Cys Lys Asp Ile Arg Trp Ser Leu
            340                 345                 350
Gly Asp Phe Gly Asp Ile Ile Met Gly Thr Asp Met Glu Gly Ile Gly
        355                 360                 365
Tyr Ser Lys Val Val Glu Asn Asn Leu Arg Ser Ile Phe Gly Thr Asp
    370                 375                 380
Glu Lys Ala Gln Gln Arg Arg Lys Gln Trp Trp Asn Glu Ser Lys Ala
385                 390                 395                 400
Gln Ile Trp Thr Ala Met Met Tyr Ser Val Lys Lys Arg Leu Lys Gly
                405                 410                 415
Asn Phe Ile Trp Ile Cys Lys Leu Asn Val Ala Val Asn Ile Glu Pro
            420                 425                 430
Gln Ile Tyr Arg Trp Ile Arg Glu Trp Gly Arg Asp Tyr Val Ser Glu
        435                 440                 445
Leu Pro Thr Glu Val Gln Lys Leu Lys Glu Lys Cys Asp Gly Lys Ile
    450                 455                 460
Asn Tyr Thr Asp Lys Lys Val Cys Lys Val Pro Pro Cys Gln Asn Ala
465                 470                 475                 480
Cys Lys Ser Tyr Asp Gln Trp Ile Thr Arg Lys Lys Asn Gln Trp Asp
                485                 490                 495
Val Leu Ser Asn Lys Phe Ile Ser Val Lys Asn Ala Glu Lys Val Gln
            500                 505                 510
Thr Ala Gly Ile Val Thr Pro Tyr Asp Ile Leu Lys Gln Glu Leu Asp
        515                 520                 525
Glu Phe Asn Glu Val Ala Phe Glu Asn Glu Ile Asn Lys Arg Asp Gly
    530                 535                 540
Ala Tyr Ile Glu Leu Cys Val Cys Ser Val Glu Glu Ala Lys Lys Asn
545                 550                 555                 560
Thr Gln Glu Val Val Thr Asn Val Asp Asn Ala Ala Lys Ser Gln Ala
                565                 570                 575
Thr Asn Ser Asn Pro Ile Ser Gln Pro Val Asp Ser Ser Lys Ala Glu
            580                 585                 590
Lys Val Pro Gly Asp Ser Thr His Gly Asn Val Asn Ser Gly Gln Asp
        595                 600                 605
```

```
Ser Ser Thr Thr Gly Lys Ala Val Thr Gly Asp Gly Gln Asn Gly Asn
    610             615                 620

Gln Thr Pro Ala Glu Ser Asp Val Gln Arg Ser Asp Ile Ala Glu Ser
625             630                 635                 640

Val Ser Ala Lys Asn Val Asp Pro Gln Lys Ser Val Ser Lys Arg Ser
            645                 650                 655

Asp Asp Thr Ala Ser Val Thr Gly Ile Ala Glu Ala Gly Lys Glu Asn
            660                 665                 670

Leu Gly Ala Ser Asn Ser Arg Pro Ser Glu Ser Thr Val Glu Ala Asn
        675                 680                 685

Ser Pro Gly Asp Asp Thr Val Asn Ser Ala Ser Ile Pro Val Val Ser
    690                 695                 700

Gly Glu Asn Pro Leu Val Thr Pro Tyr Asn Gly Leu Arg His Ser Lys
705             710                 715                 720

Asp Asn Ser Asp Ser Asp Gly Pro Ala Glu Ser Met Ala Asn Pro Asp
                725                 730                 735

Ser Asn Ser Lys Gly Glu Thr Gly Lys Gly Gln Asp Asn Asp Met Ala
            740                 745                 750

Lys Ala Thr Lys Asp Ser Ser Asn Ser Ser Asp Gly Thr Ser Ser Ala
            755                 760                 765

Thr Gly Asp Thr Thr Asp Ala Val Asp Arg Glu Ile Asn Lys Gly Val
770             775                 780

Pro Glu Asp Arg Asp Lys Thr Val Gly Ser Lys Asp Gly Gly Gly Glu
785             790                 795                 800

Asp Asn Ser Ala Asn Lys Asp Ala Ala Thr Val Val Gly Glu Asp Arg
            805                 810                 815

Ile Arg Glu Asn Ser Ala Gly Ser Thr Asn Asp Arg Ser Lys Asn
            820                 825                 830

Asp Thr Glu Lys Asn Gly Ala Ser Thr Pro Asp Ser Lys Gln Ser Glu
            835                 840                 845

Asp Ala Thr Ala Leu Ser Lys Thr Glu Ser Leu Glu Ser Thr Glu Ser
    850                 855                 860

Gly Asp Arg Thr Thr Asn Asp Thr Thr Asn Ser Leu Glu Asn Lys Asn
865             870                 875                 880

Gly Gly Lys Glu Lys Asp Leu Gln Lys His Asp Phe Lys Ser Asn Asp
                885                 890                 895

Thr Pro Asn Glu Glu Pro Asn Ser Asp Gln Thr Thr Asp Ala Glu Gly
            900                 905                 910

His Asp Arg Asp Ser Ile Lys Asn Asp Lys Ala Glu Arg Arg Lys His
    915                 920                 925

Met Asn Lys Asp Thr Phe Thr Lys Asn Thr Asn Ser His His Leu Asn
    930                 935                 940

Ser Asn Asn Asn Leu Ser Asn Gly Lys Leu Asp Ile Lys Glu Tyr Lys
945             950                 955                 960

Tyr Arg Asp Val Lys Ala Thr Arg Glu Asp Ile Ile Leu Met Ser Ser
            965                 970                 975

Val Arg Lys Cys Asn Asn Asn Ile Ser Leu Glu Tyr Cys Asn Ser Val
            980                 985                 990

Glu Asp Lys Ile Ser Ser Asn Thr Cys Ser Arg Glu Lys Ser Lys Asn
            995                 1000                1005

Leu Cys Cys Ser Ile Ser Asp Phe Cys Leu Asn Tyr Phe Asp Val Tyr
    1010            1015                1020

Ser Tyr Glu Tyr Leu Ser Cys Met Lys Lys Glu Phe Glu Asp Pro Ser
```

```
1025                1030                1035                1040
Tyr Lys Cys Phe Thr Lys Gly Gly Phe Lys Ile Asp Lys Thr Tyr Phe
                1045                1050                1055

Ala Ala Ala Gly Ala Leu Leu Ile Leu Leu Leu Ile Ala Ser Arg Lys
                1060                1065                1070

Met Ile Lys Asn Asp Ser Glu Glu Ala Thr Phe Asn Glu Phe Glu Glu
        1075                1080                1085

Tyr Cys Asp Asn Ile His Arg Ile Pro Leu Met Pro Asn Asn Ile Glu
    1090                1095                1100

His Met Gln Pro Ser Thr Pro Leu Asp Tyr Ser
1105                1110                1115
```

(2) INFORMATION FOR SEQ ID NO: 3:

(i) SEQUENCE CHARACTERISTICS:
        (A) LENGTH: 4507 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO: 3:

```
TATATATATA TATATATATA GATAATAACA TATAAATATA TTCAATGTGC ATACAATGAA      60

ATGTAATATT AGTATATATT TTTTTGCTTC CTTCTTTGTG TTATATTTTG CAAAAGCTAG     120

GAATGAATAT GATATAAAAG AGAATGAAAA ATTTTTAGAC GTGTATAAAG AAAAATTTAA     180

TGAATTAGAT AAAAGAAAT ATGGAAATGT TCAAAAAACT GATAAGAAAA TATTTACTTT     240

TATAGAAAAT AAATTAGATA TTTTAAATAA TTCAAAATTT AATAAAAGAT GGAAGAGTTA     300

TGGAACTCCA GATAATATAG ATAAAAATAT GTCTTTAATA AATAAACATA ATAATGAAGA     360

AATGTTTAAC AACAATTATC AATCATTTTT ATCGACAAGT TCATTAATAA AGCAAAATAA     420

ATATGTTCCT ATTAACGCTG TACGTGTGTC TAGGATATTA AGTTTCCTGG ATTCTAGAAT     480

TAATAATGGA AGAAATACTT CATCTAATAA CGAAGTTTTA AGTAATTGTA GGGAAAAAAG     540

GAAAGGAATG AAATGGGATT GTAAAAAGAA AAATGATAGA AGCAACTATG TATGTATTCC     600

TGATCGTAGA ATCCAATTAT GCATTGTTAA TCTTAGCATT ATTAAAACAT ATACAAAAGA     660

GACCATGAAG GATCATTTCA TTGAAGCCTC TAAAAAAGAA TCTCAACTTT TGCTTAAAAA     720

AAATGATAAC AAATATAATT CTAAATTTTG TAATGATTTG AAGAATAGTT TTTTAGATTA     780

TGGACATCTT GCTATGGGAA ATGATATGGA TTTTGGAGGT TATTCAACTA AGGCAGAAAA     840

CAAAATTCAA GAAGTTTTTA AAGGGGCTCA TGGGGAAATA AGTGAACATA AAATTAAAAA     900

TTTTAGAAAA GAATGGTGGA ATGAATTTAG AGAAACTT TGGAAGCTA TGTTATCTGA     960

GCATAAAAAT AATATAAATA ATTGTAAAAA TATTCCCCAA GAAGAATTAC AAATTACTCA    1020

ATGGATAAAA GAATGGCATG GAGAATTTTT GCTTGAAAGA GATAATAGAT CAAAATTGCC    1080

AAAAAGTAAA TGTAAAAATA ATACATTATA TGAAGCATGT GAGAAGGAAT GTATTGATCC    1140

ATGTATGAAA TATAGAGATT GGATTATTAG AAGTAAATTT GAATGGCATA CGTTATCGAA    1200

AGAATATGAA ACTCAAAAAG TTCCAAAGGA AAATGCGGAA AATTATTTAA TCAAATTTC    1260

AGAAAACAAG AATGATGCTA AAGTAAGTTT ATTATTGAAT AATTGTGATG CTGAATATTC    1320
```

```
AAAATATTGT GATTGTAAAC ATACTACTAC TCTCGTTAAA AGCGTTTTAA ATGGTAACGA    1380

CAATACAATT AAGGAAAAGC GTGAACATAT TGATTTAGAT GATTTTTCTA AATTTGGATG    1440

TGATAAAAAT TCCGTTGATA CAAACACAAA GGTGTGGGAA TGTAAAAACC CTTATATATT    1500

ATCCACTAAA GATGTATGTG TACCTCCGAG GAGGCAAGAA TTATGTCTTG GAAACATTGA    1560

TAGAATATAC GATAAAAACC TATTAATGAT AAAAGAGCAT ATTCTTGCTA TTGCAATATA    1620

TGAATCAAGA ATATTGAAAC GAAAATATAA GAATAAAGAT GATAAAGAAG TTTGTAAAAT    1680

CATAAATAAA ACTTTCGCTG ATATAAGAGA TATTATAGGA GGTACTGATT ATTGGAATGA    1740

TTTGAGCAAT AGAAAATTAG TAGGAAAAAT TAACACAAAT TCAAATATG TTCACAGGAA     1800

TAAAAAAAAT GATAAGCTTT TTCGTGATGA GTGGTGGAAA GTTATTAAAA AGATGTATG    1860

GAATGTGATA TCATGGGTAT TCAAGGATAA AACTGTTTGT AAAGAAGATG ATATTGAAAA    1920

TATACCACAA TTCTTCAGAT GGTTTAGTGA ATGGGGTGAT GATTATTGCC AGGATAAAAC    1980

AAAAATGATA GAGACTCTGA AGGTTGAATG CAAAGAAAAA CCTTGTGAAG ATGACAATTG    2040

TAAAAGTAAA TGTAATTCAT ATAAAGAATG GATATCAAAA AAAAAGAAG AGTATAATAA     2100

ACAAGCCAAA CAATACCAAG AATATCAAAA AGGAAATAAT TACAAAATGT ATTCTGAATT    2160

TAAATCTATA AAACCAGAAG TTTATTTAAA GAAATACTCG GAAAAATGTT CTAACCTAAA    2220

TTTCGAAGAT GAATTTAAGG AAGAATTACA TTCAGATTAT AAAAATAAAT GTACGATGTG    2280

TCCAGAAGTA AAGGATGTAC CAATTTCTAT AATAAGAAAT AATGAACAAA CTTCGCAAGA    2340

AGCAGTTCCT GAGGAAAACA CTGAAATAGC ACACAGAACG GAAACTCCAT CTATCTCTGA    2400

AGGACCAAAA GGAAATGAAC AAAAAGAACG TGATGACGAT AGTTTGAGTA AATAAGTGT    2460

ATCACCGAA AATTCAAGAC CTGAAACTGA TGCTAAAGAT ACTTCTAACT TGTTAAAATT     2520

AAAAGGAGAT GTTGATATTA GTATGCCTAA AGCAGTTATT GGGAGCAGTC CTAATGATAA    2580

TATAAATGTT ACTGAACAAG GGGATAATAT TTCCGGGGTG AATTCTAAAC CTTTATCTGA    2640

TGATGTACGT CCAGATAAAA AGGAATTAGA AGATCAAAAT AGTGATGAAT CGGAAGAAAC    2700

TGTAGTAAAT CATATATCAA AAAGTCCATC TATAAATAAT GGAGATGATT CAGGCAGTGG    2760

AAGTGCAACA GTGAGTGAAT CTAGTAGTTC AAATACTGGA TTGTCTATTG ATGATGATAG    2820

AAATGGTGAT ACATTTGTTC GAACACAAGA TACAGCAAAT ACTGAAGATG TTATTAGAAA    2880

AGAAAATGCT GACAAGGATG AAGATGAAAA AGGCGCAGAT GAAGAAAGAC ATAGTACTTC    2940

TGAAAGCTTA AGTTCACCTG AAGAAAAAAT GTTAACTGAT AATGAAGGAG GAAATAGTTT    3000

AAATCATGAA GAGGTGAAAG AACATACTAG TAATTCTGAT AATGTTCAAC AGTCTGGAGG    3060

AATTGTTAAT ATGAATGTTG AGAAAGAACT AAAAGATACT TTAGAAAATC CTTCTAGTAG    3120

CTTGGATGAA GGAAAAGCAC ATGAAGAATT ATCAGAACCA AATCTAAGCA GTGACCAAGA    3180

TATGTCTAAT ACACCTGGAC CTTTGGATAA CACCAGTGAA GAAACTACAG AAAGAATTAG    3240

TAATAATGAA TATAAAGTTA ACGAGAGGGA AGATGAGAGA ACGCTTACTA AGGAATATGA    3300

AGATATTGTT TTGAAAAGTC ATATGAATAG AGAATCAGAC GATGGTGAAT TATATGACGA    3360

AAATTCAGAC TTATCTACTG TAAATGATGA ATCAGAAGAC GCTGAAGCAA AAATGAAAGG    3420

AAATGATACA TCTGAAATGT CGCATAATAG TAGTCAACAT ATTGAGAGTG ATCAACAGAA    3480

AAACGATATG AAAACTGTTG GTGATTTGGG AACCACACAT GTACAAAACG AAATTAGTGT    3540

TCCTGTTACA GGAGAAATTG ATGAAAAATT AAGGGAAAGT AAAGAATCAA AAATTCATAA    3600

GGCTGAAGAG GAAAGATTAA GTCATACAGA TATACATAAA ATTAATCCTG AAGATAGAAA    3660

TAGTAATACA TTACATTTAA AAGATATAAG AAATGAGGAA AACGAAAGAC ACTTAACTAA    3720
```

-continued

```
TCAAAACATT AATATTAGTC AAGAAAGGGA TTTGCAAAAA CATGGATTCC ATACCATGAA    3780

TAATCTACAT GGAGATGGAG TTTCCGAAAG AAGTCAAATT AATCATAGTC ATCATGGAAA    3840

CAGACAAGAT CGGGGGGGAA ATTCTGGGAA TGTTTTAAAT ATGAGATCTA ATAATAATAA    3900

TTTTAATAAT ATTCCAAGTA GATATAATTT ATATGATAAA AAATTAGATT TAGATCTTTA    3960

TGAAAACAGA AATGATAGTA CAACAAAAGA ATTAATAAAG AAATTAGCAG AAATAAATAA    4020

ATGTGAGAAC GAAATTTCTG TAAAATATTG TGACCATATG ATTCATGAAG AAATCCCATT    4080

AAAAACATGC ACTAAAGAAA AAACAAGAAA TCTGTGTTGT GCAGTATCAG ATTACTGTAT    4140

GAGCTATTTT ACATATGATT CAGAGGAATA TTATAATTGT ACGAAAAGGG AATTTGATGA    4200

TCCATCTTAT ACATGTTTCA GAAAGGAGGC TTTTTCAAGT ATGATATTCA AATTTTTAAT    4260

AACAAATAAA ATATATTATT ATTTTTATAC TTACAAAACT GCAAAAGTAA CAATAAAAAA    4320

AATTAATTTC TCATTAATTT TTTTTTTCTT TTTTTCTTTT TAGGTATGCC ATATTATGCA    4380

GGAGCAGGTG TGTTATTTAT TATATTGGTT ATTTTAGGTG CTTCACAAGC CAAATATCAA    4440

AGGTTAGAAA AAATAAATAA AAATAAAATT GAGAAGAATG TAAATTAAAT ATAGAATTCG    4500

AGCTCGG                                                              4507
```

(2) INFORMATION FOR SEQ ID NO: 4:

(i) SEQUENCE CHARACTERISTICS:
        (A) LENGTH: 1435 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO: 4:

```
Met Lys Cys Asn Ile Ser Ile Tyr Phe Phe Ala Ser Phe Phe Val Leu
 1               5                  10                  15

Tyr Phe Ala Lys Ala Arg Asn Glu Tyr Asp Ile Lys Glu Asn Glu Lys
            20                  25                  30

Phe Leu Asp Val Tyr Lys Glu Lys Phe Asn Glu Leu Asp Lys Lys Lys
        35                  40                  45

Tyr Gly Asn Val Gln Lys Thr Asp Lys Lys Ile Phe Thr Phe Ile Glu
    50                  55                  60

Asn Lys Leu Asp Ile Leu Asn Asn Ser Lys Phe Asn Lys Arg Trp Lys
65                  70                  75                  80

Ser Tyr Gly Thr Pro Asp Asn Ile Asp Lys Asn Met Ser Leu Ile Asn
                85                  90                  95

Lys His Asn Asn Glu Glu Met Phe Asn Asn Tyr Gln Ser Phe Leu
            100                 105                 110

Ser Thr Ser Ser Leu Ile Lys Gln Asn Lys Tyr Val Pro Ile Asn Ala
        115                 120                 125

Val Arg Val Ser Arg Ile Leu Ser Phe Leu Asp Ser Arg Ile Asn Asn
    130                 135                 140

Gly Arg Asn Thr Ser Ser Asn Asn Glu Val Leu Ser Asn Cys Arg Glu
145                 150                 155                 160

Lys Arg Lys Gly Met Lys Trp Asp Cys Lys Lys Asn Asp Arg Ser
                165                 170                 175
```

```
Asn Tyr Val Cys Ile Pro Asp Arg Arg Ile Gln Leu Cys Ile Val Asn
            180                 185                 190
Leu Ser Ile Ile Lys Thr Tyr Thr Lys Glu Thr Met Lys Asp His Phe
        195                 200                 205
Ile Glu Ala Ser Lys Lys Glu Ser Gln Leu Leu Lys Lys Asn Asp
    210                 215                 220
Asn Lys Tyr Asn Ser Lys Phe Cys Asn Asp Leu Lys Asn Ser Phe Leu
225                 230                 235                 240
Asp Tyr Gly His Leu Ala Met Gly Asn Asp Met Asp Phe Gly Gly Tyr
                245                 250                 255
Ser Thr Lys Ala Glu Asn Lys Ile Gln Glu Val Phe Lys Gly Ala His
            260                 265                 270
Gly Glu Ile Ser Glu His Lys Ile Lys Asn Phe Arg Lys Glu Trp Trp
            275                 280                 285
Asn Glu Phe Arg Glu Lys Leu Trp Glu Ala Met Leu Ser Glu His Lys
        290                 295                 300
Asn Asn Ile Asn Asn Cys Lys Asn Ile Pro Gln Glu Glu Leu Gln Ile
305                 310                 315                 320
Thr Gln Trp Ile Lys Glu Trp His Gly Glu Phe Leu Leu Glu Arg Asp
                325                 330                 335
Asn Arg Ser Lys Leu Pro Lys Ser Lys Cys Lys Asn Asn Thr Leu Tyr
            340                 345                 350
Glu Ala Cys Glu Lys Glu Cys Ile Asp Pro Cys Met Lys Tyr Arg Asp
            355                 360                 365
Trp Ile Ile Arg Ser Lys Phe Glu Trp His Thr Leu Ser Lys Glu Tyr
        370                 375                 380
Glu Thr Gln Lys Val Pro Lys Glu Asn Ala Glu Asn Tyr Leu Ile Lys
385                 390                 395                 400
Ile Ser Glu Asn Lys Asn Asp Ala Lys Val Ser Leu Leu Leu Asn Asn
                405                 410                 415
Cys Asp Ala Glu Tyr Ser Lys Tyr Cys Asp Cys Lys His Thr Thr Thr
            420                 425                 430
Leu Val Lys Ser Val Leu Asn Gly Asn Asp Asn Thr Ile Lys Glu Lys
        435                 440                 445
Arg Glu His Ile Asp Leu Asp Asp Phe Ser Lys Phe Gly Cys Asp Lys
    450                 455                 460
Asn Ser Val Asp Thr Asn Thr Lys Val Trp Glu Cys Lys Asn Pro Tyr
465                 470                 475                 480
Ile Leu Ser Thr Lys Asp Val Cys Val Pro Pro Arg Arg Gln Glu Leu
                485                 490                 495
Cys Leu Gly Asn Ile Asp Arg Ile Tyr Asp Lys Asn Leu Leu Met Ile
            500                 505                 510
Lys Glu His Ile Leu Ala Ile Ala Ile Tyr Glu Ser Arg Ile Leu Lys
        515                 520                 525
Arg Lys Tyr Lys Asn Lys Asp Asp Lys Glu Val Cys Lys Ile Ile Asn
    530                 535                 540
Lys Thr Phe Ala Asp Ile Arg Asp Ile Ile Gly Gly Thr Asp Tyr Trp
545                 550                 555                 560
Asn Asp Leu Ser Asn Arg Lys Leu Val Gly Lys Ile Asn Thr Asn Ser
                565                 570                 575
Lys Tyr Val His Arg Asn Lys Lys Asn Asp Lys Leu Phe Arg Asp Glu
            580                 585                 590
```

-continued

| | | | | | | | | | | | |
|---|---|---|---|---|---|---|---|---|---|---|---|
|Trp|Trp|Lys|Val|Ile|Lys|Lys|Asp|Val|Trp|Asn|Val|Ile|Ser|Trp|Val|
| |595| | | |600| | | |605| | | | | | |

Phe Lys Asp Lys Thr Val Cys Lys Glu Asp Asp Ile Glu Asn Ile Pro
    610               615              620

Gln Phe Phe Arg Trp Phe Ser Glu Trp Gly Asp Tyr Cys Gln Asp
625             630              635            640

Lys Thr Lys Met Ile Glu Thr Leu Lys Val Glu Cys Lys Glu Lys Pro
             645              650            655

Cys Glu Asp Asp Asn Cys Lys Ser Lys Cys Asn Ser Tyr Lys Glu Trp
        660             665            670

Ile Ser Lys Lys Lys Glu Glu Tyr Asn Lys Gln Ala Lys Gln Tyr Gln
         675             680            685

Glu Tyr Gln Lys Gly Asn Asn Tyr Lys Met Tyr Ser Glu Phe Lys Ser
     690             695            700

Ile Lys Pro Glu Val Tyr Leu Lys Lys Tyr Ser Glu Lys Cys Ser Asn
705             710              715            720

Leu Asn Phe Glu Asp Glu Phe Lys Glu Glu Leu His Ser Asp Tyr Lys
             725              730            735

Asn Lys Cys Thr Met Cys Pro Glu Val Lys Asp Val Pro Ile Ser Ile
        740            745            750

Ile Arg Asn Asn Glu Gln Thr Ser Gln Glu Ala Val Pro Glu Glu Asn
     755             760            765

Thr Glu Ile Ala His Arg Thr Glu Thr Pro Ser Ile Ser Glu Gly Pro
    770              775            780

Lys Gly Asn Glu Gln Lys Glu Arg Asp Asp Ser Leu Ser Lys Ile
785             790              795            800

Ser Val Ser Pro Glu Asn Ser Arg Pro Glu Thr Asp Ala Lys Asp Thr
        805            810            815

Ser Asn Leu Leu Lys Leu Lys Gly Asp Val Asp Ile Ser Met Pro Lys
         820             825            830

Ala Val Ile Gly Ser Ser Pro Asn Asp Asn Ile Asn Val Thr Glu Gln
             835              840            845

Gly Asp Asn Ile Ser Gly Val Asn Ser Lys Pro Leu Ser Asp Asp Val
     850             855            860

Arg Pro Asp Lys Lys Glu Leu Glu Asp Gln Asn Ser Asp Glu Ser Glu
865             870              875            880

Glu Thr Val Val Asn His Ile Ser Lys Ser Pro Ser Ile Asn Asn Gly
             885              890            895

Asp Asp Ser Gly Ser Gly Ser Ala Thr Val Ser Glu Ser Ser Ser Ser
        900            905            910

Asn Thr Gly Leu Ser Ile Asp Asp Asp Arg Asn Gly Asp Thr Phe Val
        915            920            925

Arg Thr Gln Asp Thr Ala Asn Thr Glu Asp Val Ile Arg Lys Glu Asn
930             935              940

Ala Asp Lys Asp Glu Asp Glu Lys Gly Ala Asp Glu Glu Arg His Ser
945             950              955            960

Thr Ser Glu Ser Leu Ser Ser Pro Glu Glu Lys Met Leu Thr Asp Asn
             965              970            975

Glu Gly Gly Asn Ser Leu Asn His Glu Glu Val Lys Glu His Thr Ser
        980            985            990

Asn Ser Asp Asn Val Gln Gln Ser Gly Gly Ile Val Asn Met Asn Val
        995           1000          1005

Glu Lys Glu Leu Lys Asp Thr Leu Glu Asn Pro Ser Ser Ser Leu Asp

```
                      1010                1015                1020
Glu Gly Lys Ala His Glu Glu Leu Ser Glu Pro Asn Leu Ser Ser Asp
1025                1030                1035                1040

Gln Asp Met Ser Asn Thr Pro Gly Pro Leu Asp Asn Thr Ser Glu Glu
                1045                1050                1055

Thr Thr Glu Arg Ile Ser Asn Asn Glu Tyr Lys Val Asn Glu Arg Glu
            1060                1065                1070

Asp Glu Arg Thr Leu Thr Lys Glu Tyr Glu Asp Ile Val Leu Lys Ser
        1075                1080                1085

His Met Asn Arg Glu Ser Asp Asp Gly Glu Leu Tyr Asp Glu Asn Ser
    1090                1095                1100

Asp Leu Ser Thr Val Asn Asp Glu Ser Glu Asp Ala Glu Ala Lys Met
1105                1110                1115                1120

Lys Gly Asn Asp Thr Ser Glu Met Ser His Asn Ser Ser Gln His Ile
                1125                1130                1135

Glu Ser Asp Gln Gln Lys Asn Asp Met Lys Thr Val Gly Asp Leu Gly
            1140                1145                1150

Thr Thr His Val Gln Asn Glu Ile Ser Val Pro Val Thr Gly Glu Ile
        1155                1160                1165

Asp Glu Lys Leu Arg Glu Ser Lys Glu Ser Lys Ile His Lys Ala Glu
    1170                1175                1180

Glu Glu Arg Leu Ser His Thr Asp Ile His Lys Ile Asn Pro Glu Asp
1185                1190                1195                1200

Arg Asn Ser Asn Thr Leu His Leu Lys Asp Ile Arg Asn Glu Glu Asn
                1205                1210                1215

Glu Arg His Leu Thr Asn Gln Asn Ile Asn Ile Ser Gln Glu Arg Asp
            1220                1225                1230

Leu Gln Lys His Gly Phe His Thr Met Asn Asn Leu His Gly Asp Gly
        1235                1240                1245

Val Ser Glu Arg Ser Gln Ile Asn His Ser His His Gly Asn Arg Gln
    1250                1255                1260

Asp Arg Gly Gly Asn Ser Gly Asn Val Leu Asn Met Arg Ser Asn Asn
1265                1270                1275                1280

Asn Asn Phe Asn Asn Ile Pro Ser Arg Tyr Asn Leu Tyr Asp Lys Lys
                1285                1290                1295

Leu Asp Leu Asp Leu Tyr Glu Asn Arg Asn Asp Ser Thr Thr Lys Glu
            1300                1305                1310

Leu Ile Lys Lys Leu Ala Glu Ile Asn Lys Cys Glu Asn Glu Ile Ser
        1315                1320                1325

Val Lys Tyr Cys Asp His Met Ile His Glu Ile Pro Leu Lys Thr
    1330                1335                1340

Cys Thr Lys Glu Lys Thr Arg Asn Leu Cys Cys Ala Val Ser Asp Tyr
1345                1350                1355                1360

Cys Met Ser Tyr Phe Thr Tyr Asp Ser Glu Glu Tyr Tyr Asn Cys Thr
                1365                1370                1375

Lys Arg Glu Phe Asp Asp Pro Ser Tyr Thr Cys Phe Arg Lys Glu Ala
            1380                1385                1390

Phe Ser Ser Met Ile Phe Lys Phe Leu Ile Thr Asn Lys Ile Tyr Tyr
        1395                1400                1405

Tyr Phe Tyr Thr Tyr Lys Thr Ala Lys Val Thr Ile Lys Lys Ile Asn
    1410                1415                1420

Phe Ser Leu Ile Phe Phe Phe Phe Ser Phe
1425                1430                1435
```

(2) INFORMATION FOR SEQ ID NO: 5:

(i) SEQUENCE CHARACTERISTICS:
        (A) LENGTH: 2288 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO: 5:

```
CACTTTATGC TTCCGGCTCG TATGTTGTGT GGAATTGTGA GCGGATAACA ATTTCACACA      60
GGAAACAGCT ATGACCATGA TTACGCCAAG CTCTAATACG ACTCACTATA GGGAAAGCTG     120
GTACGCCTGC AGGTCCGGTC CGGAATTCAA TAAAATATTT CCAGAAAGGA ATGTGCAAAT     180
TCACATATCC AATATATTCA AGGAATATAA AGAAATAAT GTAGATATCA TATTTGGAAC      240
GTTGAATTAT GAATATAATA ATTTCTGTAA AGAAAAACCT GAATTAGTAT CTGCTGCCAA     300
GTATAATCTG AAAGCTCCAA ATGCTAAATC CCCTAGAATA TACAAATCTA AGGAGCATGA     360
AGAATCAAGT GTGTTTGGTT GCAAAACGAA AATCAGTAAA GTTAAAAAAA AATGGAATTG     420
TTATAGTAAT AATAAAGTAA CTAAACCTGA AGGTGTATGT GGACCACCAA GAAGGCAACA     480
ATTATGTCTT GGATATATAT TTTTGATTCG CGACGGTAAC GAGGAAGGAT TAAAAGATCA     540
TATTAATAAG GCAGCTAATT ATGAGGCAAT GCATTTAAAA GAGAAATATG AGAATGCTGG     600
TGGTGATAAA ATTTGCAATG CTATATTGGG AAGTTATGCA GATATTGGAG ATATTGTAAG     660
AGGTTTGGAT GTTTGGAGGG ATATAAATAC TAATAAATTA TCAGAAAAAT TCCAAAAAAT     720
TTTTATGGGT GGTGGTAATT CTAGGAAAAA ACAAAACGAT AATAATGAAC GTAATAAATG     780
GTGGGAAAAA CAAGGAATT TAATATGGTC TAGTATGGTA AAACACATTC CAAAAGGAAA     840
AACATGTAAA CGTCATAATA ATTTTGAGAA AATTCCTCAA TTTTTGAGAT GGTTAAAAGA     900
ATGGGGTGAT GAATTTTGTG AGGAAATGGG TACGGAAGTC AAGCAATTAG AGAAAATATG     960
TGAAAATAAA AATTGTTCGG AAAAAAAATG TAAAAATGCA TGTAGTTCCT ATGAAAAATG    1020
GATAAAGGAA CGAAAAAATG AATATAATTT GCAATCAAAG AAATTTGATA GTGATAAAAA    1080
ATTAAATAAA AAAACAATC TTTATAATAA ATTTGAGGAT TCTAAAGCTT ATTTAAGGAG     1140
TGAATCAAAA CAGTGCTCAA ATATAGAATT TAATGATGAA ACATTTACAT TCCTAATAA     1200
ATATAAAGAG GCTTGTATGG TATGTGAAAA TCCTTCATCT TCGAAAGCTC TTAAACCTAT    1260
AAAAACGAAT GTGTTTCCTA TAGAGGAATC AAAAAAATCT GAGTTATCAA GTTTAACAGA    1320
TAAATCTAAG AATACTCCTA ATAGTTCTGG TGGGGGAAAT TATGGAGATA GACAAATATC    1380
AAAAAGAGAC GATGTTCATC ATGATGGTCC TAAGGAAGTG AAATCCGGAG AAAAAGAGGT    1440
ACCAAAAATA GATGCAGCTG TTAAAACAGA AAATGAATTT ACCTCTAATC GAACGATAT     1500
TGAAGGAAAG GAAAAAGTA AGGTGATCA TTCTTCTCCT GTTCATTCTA AAGATATAAA      1560
AAATGAGGAA CCACAAAGGG TGGTGTCTGA AATTTACCT AAAATTGAAG AGAAAATGGA     1620
ATCTTCTGAT TCTATACCAA TTACTCATAT AGAAGCTGAA AAGGGTCAGT CTTCTAATTC    1680
TAGCGATAAT GATCCTGCAG TAGTAAGTGG TAGAGAATCT AAAGATGTAA ATCTTCATAC    1740
TTCTGAAAGG ATTAAAGAAA ATGAAGAAGG TGTGATTAAA ACAGATGATA GTTCAAAAAG    1800
```

-continued

```
TATTGAAATT TCTAAAATAC CATCTGACCA AAATAATCAT AGTGATTTAT CACAGAATGC      1860

AAATGAGGAC TCTAATCAAG GGAATAAGGA AACAATAAAT CCTCCTTCTA CAGAAAAAAA      1920

TCTCAAAGAA ATTCATTATA AAACATCTGA TTCTGATGAT CATGGTTCTA AAATTAAAAG      1980

TGAAATTGAA CCAAAGGAGT TAACGGAGGA ATCACCTCTT ACTGATAAAA AAACTGAAAG      2040

TGCAGCGATT GGTGATAAAA ATCATGAATC AGTAAAAAGC GCTGATATTT TCAATCTGA       2100

GATTCATAAT TCTGATAATA GAGATAGAAT TGTTTCTGAA AGTGTAGTTC AGGATTCTTC      2160

AGGAAGCTCT ATGAGTACTG AATCTATACG TACTGATAAC AAGGATTTTA AAACAAGTGA      2220

GGATATTGCA CCTTCTATTA ATGGTCGGAA TTCCCGGGTC GACGAGCTCA CTAGTCGGCG      2280

GCCGCTCT                                                              2288
```

(2) INFORMATION FOR SEQ ID NO: 6:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO: 6:

```
Ala Asp Asn Asn Phe Thr Gln Glu Thr Ala Met Thr Met Ile Thr Pro
1               5                   10                  15

Ser Ser Asn Thr Thr His Tyr Arg Glu Ser Trp Tyr Ala Cys Arg Ser
            20                  25                  30

Gly Pro Glu Phe Asn Lys Ile Phe Pro Glu Arg Asn Val Gln Ile His
        35                  40                  45

Ile Ser Asn Ile Phe Lys Glu Tyr Lys Glu Asn Asn Val Asp Ile Ile
    50                  55                  60

Phe Gly Thr Leu Asn Tyr Glu Tyr Asn Asn Phe Cys Lys Glu Lys Pro
65                  70                  75                  80

Glu Leu Val Ser Ala Ala Lys Tyr Asn Leu Lys Ala Pro Asn Ala Lys
                85                  90                  95

Ser Pro Arg Ile Tyr Lys Ser Lys Glu His Glu Glu Ser Ser Val Phe
            100                 105                 110

Gly Cys Lys Thr Lys Ile Ser Lys Val Lys Lys Trp Asn Cys Tyr
        115                 120                 125

Ser Asn Asn Lys Val Thr Lys Pro Glu Gly Val Cys Gly Pro Pro Arg
    130                 135                 140

Arg Gln Gln Leu Cys Leu Gly Tyr Ile Phe Leu Ile Arg Asp Gly Asn
145                 150                 155                 160

Glu Glu Gly Leu Lys Asp His Ile Asn Lys Ala Ala Asn Tyr Glu Ala
                165                 170                 175

Met His Leu Lys Glu Lys Tyr Glu Asn Ala Gly Gly Asp Lys Ile Cys
            180                 185                 190

Asn Ala Ile Leu Gly Ser Tyr Ala Asp Ile Gly Asp Ile Val Arg Gly
        195                 200                 205

Leu Asp Val Trp Arg Asp Ile Asn Thr Asn Lys Leu Ser Glu Lys Phe
    210                 215                 220

Gln Lys Ile Phe Met Gly Gly Gly Asn Ser Arg Lys Lys Gln Asn Asp
```

-continued

```
                225                 230                 235                 240
Asn Asn Glu Arg Asn Lys Trp Trp Glu Lys Gln Arg Asn Leu Ile Trp
                    245                 250                 255
Ser Ser Met Val Lys His Ile Pro Lys Gly Lys Thr Cys Lys Arg His
                260                 265                 270
Asn Asn Phe Glu Lys Ile Pro Gln Phe Leu Arg Trp Leu Lys Glu Trp
                275                 280                 285
Gly Asp Glu Phe Cys Glu Met Gly Thr Glu Val Lys Gln Leu Glu
            290                 295                 300
Lys Ile Cys Glu Asn Lys Asn Cys Ser Glu Lys Cys Lys Asn Ala
305                 310                 315                 320
Cys Ser Ser Tyr Glu Lys Trp Ile Lys Glu Arg Lys Asn Glu Tyr Asn
                    325                 330                 335
Leu Gln Ser Lys Lys Phe Asp Ser Asp Lys Lys Leu Asn Lys Lys Asn
                340                 345                 350
Asn Leu Tyr Asn Lys Phe Glu Asp Ser Lys Ala Tyr Leu Arg Ser Glu
            355                 360                 365
Ser Lys Gln Cys Ser Asn Ile Glu Phe Asn Asp Glu Thr Phe Thr Phe
        370                 375                 380
Pro Asn Lys Tyr Lys Glu Ala Cys Met Val Cys Glu Asn Pro Ser Ser
385                 390                 395                 400
Ser Lys Ala Leu Lys Pro Ile Lys Thr Asn Val Phe Pro Ile Glu Glu
                    405                 410                 415
Ser Lys Lys Ser Glu Leu Ser Ser Leu Thr Asp Lys Ser Lys Asn Thr
                420                 425                 430
Pro Asn Ser Ser Gly Gly Gly Asn Tyr Gly Asp Arg Gln Ile Ser Lys
            435                 440                 445
Arg Asp Asp Val His His Asp Gly Pro Lys Glu Val Lys Ser Gly Glu
        450                 455                 460
Lys Glu Val Pro Lys Ile Asp Ala Ala Val Lys Thr Glu Asn Glu Phe
465                 470                 475                 480
Thr Ser Asn Arg Asn Asp Ile Glu Gly Lys Glu Lys Ser Lys Gly Asp
                    485                 490                 495
His Ser Ser Pro Val His Ser Lys Asp Ile Lys Asn Glu Glu Pro Gln
                500                 505                 510
Arg Val Val Ser Glu Asn Leu Pro Lys Ile Glu Glu Lys Met Glu Ser
            515                 520                 525
Ser Asp Ser Ile Pro Ile Thr His Ile Glu Ala Glu Lys Gly Gln Ser
        530                 535                 540
Ser Asn Ser Ser Asp Asn Asp Pro Ala Val Val Ser Gly Arg Glu Ser
545                 550                 555                 560
Lys Asp Val Asn Leu His Thr Ser Glu Arg Ile Lys Glu Asn Glu Glu
                    565                 570                 575
Gly Val Ile Lys Thr Asp Asp Ser Lys Ser Ile Glu Ile Ser Lys
                580                 585                 590
Ile Pro Ser Asp Gln Asn Asn His Ser Asp Leu Ser Gln Asn Ala Asn
            595                 600                 605
Glu Asp Ser Asn Gln Gly Asn Lys Glu Thr Ile Asn Pro Pro Ser Thr
        610                 615                 620
Glu Lys Asn Leu Lys Glu Ile His Tyr Lys Thr Ser Asp Ser Asp Asp
625                 630                 635                 640
His Gly Ser Lys Ile Lys Ser Glu Ile Glu Pro Lys Glu Leu Thr Glu
                    645                 650                 655
```

```
Glu Ser Pro Leu Thr Asp Lys Lys Thr Glu Ser Ala Ala Ile Gly Asp
            660                 665                 670

Lys Asn His Glu Ser Val Lys Ser Ala Asp Ile Phe Gln Ser Glu Ile
        675                 680                 685

His Asn Ser Asp Asn Arg Asp Arg Ile Val Ser Glu Ser Val Val Gln
        690                 695                 700

Asp Ser Ser Gly Ser Ser Met Ser Thr Glu Ser Ile Arg Thr Asp Asn
705                 710                 715                 720

Lys Asp Phe Lys Thr Ser Glu Asp Ile Ala Pro Ser Ile Asn Gly Arg
                725                 730                 735

Asn Ser Arg Val Asp Glu Leu Thr Ser Arg Arg Pro Leu
        740                 745

(2) INFORMATION FOR SEQ ID NO: 7:

(i) SEQUENCE CHARACTERISTICS:
        (A) LENGTH: 2606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO: 7:
```

| | | | | | |
|---|---|---|---|---|---|
| AGCTCTATTA | CGACTCACTA | TAGGGAAAGC | TGGTACGCCT | GCAGGTACCG | GTCCGGAATT | 60 |
| CCCGGGTCGA | CGAGCTCACT | AGTCGGCGGC | CGCTCTAGAG | GATCCAAGCT | TAATAGTGTT | 120 |
| TATACGTCTA | TTGGCTTATT | TTTAAATAGC | TTAAAAAGCG | GACCATGTAA | AAAGGATAAT | 180 |
| GATAATGCAG | AGGATAATAT | AGATTTTGGT | GATGAAGGTA | AAACATTTAA | AGAGGCAGAT | 240 |
| AATTGTAAAC | CATGTTCTCA | ATTTACTGTT | GATTGTAAAA | ATTGTAATGG | TGGTGATACA | 300 |
| AAAGGGAAGT | GCAATGGCAG | CAATGGCAAA | AGAATGGAA  | ATGATTATAT | TACTGCAAGT | 360 |
| GATATTGAAA | ATGGAGGGAA | TTCTATTGGA | AATATAGATA | TGGTTGTTAG | TGATAAGGAT | 420 |
| GCAAATGGAT | TTAATGGTTT | AGACGCTTGT | GGAAGTGCAA | ATATCTTTAA | AGGTATTAGA | 480 |
| AAAGAACAAT | GGAAATGTGC | TAAAGTATGT | GGTTTAGATG | TATGTGGTCT | TAAAAATGGT | 540 |
| AATGGTAGTA | TAGATAAAGA | TCAAAAACAA | ATTATAATTA | TTAGAGCATT | GCTTAAACGT | 600 |
| TGGGTAGAAT | ATTTTTTAGA | AGATTATAAT | AAAATTAATG | CCAAAATTTC | ACATTGTACG | 660 |
| AAAAAGGATA | ATGAATCCAC | ATGTACAAAT | GATTGTCCAA | ATAAATGTAC | ATGTGTAGAA | 720 |
| GAGTGGATAA | ATCAGAAAAG | GACAGAATGG | AAAAATATAA | AAAAACATTA | CAAAACACAA | 780 |
| AATGAAAATG | GTGACAATAA | CATGAAATCT | TTGGTTACAG | ATATTTTGGG | TGCCTTGCAA | 840 |
| CCCCAAAGTG | ATGTTAACAA | AGCTATAAAA | CCTTGTAGTG | GTTTAACTGC | GTTCGAGAGT | 900 |
| TTTTGTGGTC | TTAATGGCGC | TGATAACTCA | GAAAAAAAG  | AAGGTGAAGA | TTACGATCTT | 960 |
| GTTCTATGTA | TGCTTAAAAA | TCTTGAAAAA | CAAATTCAGG | AGTGCAAAAA | GAAACATGGC | 1020 |
| GAAACTAGTG | TCGAAAATGG | TGGCAAATCA | TGTACCCCCC | TTGACAACAC | CACCCTTGAG | 1080 |
| GAGGAACCCA | TAGAAGAGGA | AAACCAAGTG | GAAGCGCCGA | ACATTTGTCC | AAAACAAACA | 1140 |
| GTGGAAGATA | AAAAAAAGA  | GGAAGAAGAA | GAAACTTGTA | CACCGGCATC | ACCAGTACCA | 1200 |
| GAAAAACCGG | TACCTCATGT | GGCACGTTGG | CGAACATTTA | CACCACCTGA | GGTATTCAAG | 1260 |

```
ATATGGAGGG GAAGGAGAAA TAAAACTACG TGCGAAATAG TGGCAGAAAT GCTTAAAGAT    1320

AAGAATGGAA GGACTACAGT AGGTGAATGT TATAGAAAAG AAACTTATTC TGAATGGACG    1380

TGTGATGAAA GTAAGATTAA AATGGGACAG CATGGAGCAT GTATTCCTCC AAGAAGACAA    1440

AAATTATGTT TACATTATTT AGAAAAAATA ATGACAAATA CAAATGAATT GAAATACGCA    1500

TTTATTAAAT GTGCTGCAGC AGAAACTTTT TTGTTATGGC AAAACTACAA AAAGATAAG     1560

AATGGTAATG CAGAAGATCT CGATGAAAAA TTAAAAGGTG GTATTATCCC CGAAGATTTT    1620

AAACGGCAAA TGTTCTATAC GTTTGCAGAT TATAGAGATA TATGTTTGGG TACGGATATA    1680

TCATCAAAAA AAGATACAAG TAAAGGTGTA GGTAAAGTAA AATGCAATAT TGATGATGTT    1740

TTTTATAAAA TTAGCAATAG TATTCGTTAC CGTAAAAGTT GGTGGGAAAC AAATGGTCCA    1800

GTTATATGGG AAGGAATGTT ATGCGCTTTA AGTTATGATA CGAGCCTAAA TAATGTTAAT    1860

CCGGAAACTC ACAAAAAACT TACCGAAGGC AATAACAACT TTGAGAAAGT CATATTTGGT    1920

AGTGATAGTA GCACTACTTT GTCCAAATTT TCTGAAAGAC CTCAATTTCT AAGATGGTTG    1980

ACTGAATGGG GAGAAAATTT CTGCAAAGAA CAAAAAAAGG AGTATAAGGT GTTGTTGGCA    2040

AAATGTAAGG ATTGTGATGT TGATGGTGAT GGTAAATGTA ATGGAAAATG TGTTGCGTGC    2100

AAAGATCAAT GTAAACAATA TCATAGTTGG ATTGGAATAT GGATAGATAA TTATAAAAAA    2160

CAAAAAGGAA GATATACTGA GGTTAAAAAA ATACCTCTGT ATAAAGAAGA TAAAGACGTG    2220

AAAAACTCAG ATGATGCTCG CGATTATTTA AAAACACAAT TACAAAATAT GAAATGTGTA    2280

AATGGAACTA CTGATGAAAA TTGTGAGTAT AAGTGTATGC ATAAAACCTC ATCCACAAAT    2340

AGTGATATGC CCGAATCGTT GGACGAAAAG CCGGAAAAGG TCAAAGACAA GTGTAATTGT    2400

GTACCTAATG AATGCAATGC ATTGAGTGTA AGTGGTAGCG GTTTTCCTGA TGGTCAAGCT    2460

TACGTACGCG TGCATGCGAC GTCATAGCTC TTCTATAGTG TCACCTAAAT TCAATTCACT    2520

GGCCGTCGTT TTCAACGTC GTGACTGGGA AAACCTGGCG TTACCCAACT TAATCGCCTT     2580

GCAGCACATC CCCCTTTCGC CAGCTG                                        2606
```

(2) INFORMATION FOR SEQ ID NO: 8:

(i) SEQUENCE CHARACTERISTICS:
        (A) LENGTH: 921 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO: 8:

```
Lys Leu Asn Ser Val Tyr Thr Ser Ile Gly Leu Phe Leu Asn Ser Leu
1               5                   10                  15

Lys Ser Gly Pro Cys Lys Lys Asp Asn Asp Asn Ala Glu Asp Asn Ile
            20                  25                  30

Asp Phe Gly Asp Glu Gly Lys Thr Phe Lys Glu Ala Asp Asn Cys Lys
        35                  40                  45

Pro Cys Ser Gln Phe Thr Val Asp Cys Lys Asn Cys Asn Gly Gly Asp
    50                  55                  60

Thr Lys Gly Lys Cys Asn Gly Ser Asn Gly Lys Lys Asn Gly Asn Asp
65                  70                  75                  80
```

-continued

```
Tyr Ile Thr Ala Ser Asp Ile Glu Asn Gly Gly Asn Ser Ile Gly Asn
             85                  90                  95

Ile Asp Met Val Val Ser Asp Lys Asp Ala Asn Gly Phe Asn Gly Leu
            100                 105                 110

Asp Ala Cys Gly Ser Ala Asn Ile Phe Lys Gly Ile Arg Lys Glu Gln
            115                 120                 125

Trp Lys Cys Ala Lys Val Cys Gly Leu Asp Val Cys Gly Leu Lys Asn
        130                 135                 140

Gly Asn Gly Ser Ile Asp Lys Asp Gln Lys Gln Ile Ile Ile Arg
145                 150                 155                 160

Ala Leu Leu Lys Arg Trp Val Glu Tyr Phe Leu Glu Asp Tyr Asn Lys
                165                 170                 175

Ile Asn Ala Lys Ile Ser His Cys Thr Lys Lys Asp Asn Glu Ser Thr
            180                 185                 190

Cys Thr Asn Asp Cys Pro Asn Lys Cys Thr Cys Val Glu Glu Trp Ile
        195                 200                 205

Asn Gln Lys Arg Thr Glu Trp Lys Asn Ile Lys Lys His Tyr Lys Thr
    210                 215                 220

Gln Asn Glu Asn Gly Asp Asn Asn Met Lys Ser Leu Val Thr Asp Ile
225                 230                 235                 240

Leu Gly Ala Leu Gln Pro Gln Ser Asp Val Asn Lys Ala Ile Lys Pro
                245                 250                 255

Cys Ser Gly Leu Thr Ala Phe Glu Ser Phe Cys Gly Leu Asn Gly Ala
            260                 265                 270

Asp Asn Ser Glu Lys Lys Glu Gly Glu Asp Tyr Asp Leu Val Leu Cys
        275                 280                 285

Met Leu Lys Asn Leu Glu Lys Gln Ile Gln Glu Cys Lys Lys Lys His
    290                 295                 300

Gly Glu Thr Ser Val Glu Asn Gly Gly Lys Ser Cys Thr Pro Leu Asp
305                 310                 315                 320

Asn Thr Thr Leu Glu Glu Glu Pro Ile Glu Glu Asn Gln Val Glu
                325                 330                 335

Ala Pro Asn Ile Cys Pro Lys Gln Thr Val Glu Asp Lys Lys Lys Glu
            340                 345                 350

Glu Glu Glu Glu Thr Cys Thr Pro Ala Ser Pro Val Pro Glu Lys Pro
        355                 360                 365

Val Pro His Val Ala Arg Trp Arg Thr Phe Thr Pro Glu Val Phe
370                 375                 380

Lys Ile Trp Arg Gly Arg Arg Asn Lys Thr Thr Cys Glu Ile Val Ala
385                 390                 395                 400

Glu Met Leu Lys Asp Lys Asn Gly Arg Thr Thr Val Gly Glu Cys Tyr
                405                 410                 415

Arg Lys Glu Thr Tyr Ser Glu Trp Thr Cys Asp Glu Ser Lys Ile Lys
            420                 425                 430

Met Gly Gln His Gly Ala Cys Ile Pro Pro Arg Arg Gln Lys Leu Cys
        435                 440                 445

Leu His Tyr Leu Glu Lys Ile Met Thr Asn Thr Asn Glu Leu Lys Tyr
    450                 455                 460

Ala Phe Ile Lys Cys Ala Ala Glu Thr Phe Leu Leu Trp Gln Asn
465                 470                 475                 480

Tyr Lys Lys Asp Lys Asn Gly Asn Ala Glu Asp Leu Asp Glu Lys Leu
                485                 490                 495

Lys Gly Gly Ile Ile Pro Glu Asp Phe Lys Arg Gln Met Phe Tyr Thr
```

```
                    500                 505                 510
Phe Ala Asp Tyr Arg Asp Ile Cys Leu Gly Thr Asp Ile Ser Ser Lys
                515                 520                 525
Lys Asp Thr Ser Lys Gly Val Gly Lys Val Lys Cys Asn Ile Asp Asp
            530                 535                 540
Val Phe Tyr Lys Ile Ser Asn Ser Ile Arg Tyr Arg Lys Ser Trp Trp
545                 550                 555                 560
Glu Thr Asn Gly Pro Val Ile Trp Glu Gly Met Leu Cys Ala Leu Ser
                565                 570                 575
Tyr Asp Thr Ser Leu Asn Asn Val Asn Pro Glu Thr His Lys Lys Leu
            580                 585                 590
Thr Glu Gly Asn Asn Asn Phe Glu Lys Val Ile Phe Gly Ser Asp Ser
                595                 600                 605
Ser Thr Thr Leu Ser Lys Phe Ser Glu Arg Pro Gln Phe Leu Arg Trp
            610                 615                 620
Leu Thr Glu Trp Gly Glu Asn Phe Cys Lys Glu Gln Lys Lys Glu Tyr
625                 630                 635                 640
Lys Val Leu Leu Ala Lys Cys Lys Asp Cys Asp Val Asp Gly Asp Gly
                645                 650                 655
Lys Cys Asn Gly Lys Cys Val Ala Cys Lys Asp Gln Cys Lys Gln Tyr
            660                 665                 670
His Ser Trp Ile Gly Ile Trp Ile Asp Asn Tyr Lys Lys Gln Lys Gly
            675                 680                 685
Arg Tyr Thr Glu Val Lys Lys Ile Pro Leu Tyr Lys Glu Asp Lys Asp
            690                 695                 700
Val Lys Asn Ser Asp Asp Ala Arg Asp Tyr Leu Lys Thr Gln Leu Gln
705                 710                 715                 720
Asn Met Lys Cys Val Asn Gly Thr Thr Asp Glu Asn Cys Glu Tyr Lys
                725                 730                 735
Cys Met His Lys Thr Ser Ser Thr Asn Ser Asp Met Pro Glu Ser Leu
            740                 745                 750
Asp Glu Lys Pro Glu Lys Val Lys Asp Lys Cys Asn Cys Val Pro Asn
            755                 760                 765
Glu Cys Asn Ala Leu Ser Val Ser Gly Ser Gly Phe Pro Asp Gly Gln
            770                 775                 780
Ala Phe Gly Gly Gly Val Leu Glu Gly Thr Cys Lys Gly Leu Gly Glu
785                 790                 795                 800
Pro Lys Lys Lys Ile Glu Pro Pro Gln Tyr Asp Pro Thr Asn Asp Ile
                805                 810                 815
Leu Lys Ser Thr Ile Pro Val Thr Ile Val Leu Ala Leu Gly Ser Ile
            820                 825                 830
Ala Phe Leu Phe Met Lys Val Ile Tyr Ile Tyr Val Trp Tyr Ile Tyr
            835                 840                 845
Met Leu Cys Val Gly Ala Leu Asp Thr Tyr Ile Cys Gly Cys Ile Cys
        850                 855                 860
Ile Cys Ile Phe Ile Cys Val Ser Val Tyr Val Cys Val Tyr Val Tyr
865                 870                 875                 880
Val Phe Leu Tyr Met Cys Val Phe Tyr Ile Tyr Phe Ile Tyr Ile Tyr
                885                 890                 895
Val Phe Ile Leu Lys Met Lys Lys Met Lys Lys Met Lys Lys Met Lys
                900                 905                 910
Lys Met Lys Lys Arg Lys Lys Arg Ile
            915                 920
```

(2) INFORMATION FOR SEQ ID NO: 9:

(i) SEQUENCE CHARACTERISTICS:
        (A) LENGTH: 2101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO: 9:

```
GGAACAGGGT GATAATAAAG TAGGAGCCTG TGCTCCGTAT AGACGATTAC ATTTATGTGA      60

TTATAATTTG GAATCTATAG ACACAACGTC GACGACGCAT AAGTTGTTGT TAGAGGTGTG     120

TATGGCAGCA AAATACGAAG GAAACTCAAT AAATACACAT TATACACAAC ATCAACGAAC     180

TAATGAGGAT TCTGCTTCCC AATTATGTAC TGTATTAGCA CGAAGTTTTG CAGATATAGG     240

TGATATCGTA AGAGGAAAAG ATCTATATCT CGGTTATGAT AATAAAGAAA AGAACAAAG     300

AAAAAAATTA GAACAGAAAT TGAAAGATAT TTTCAAGAAA ATACATAAGG ACGTGATGAA     360

GACGAATGGC GCACAAGAAC GCTACATAGA TGATGCCAAA GGAGGAGATT TTTTTCAATT     420

AAGAGAAGAT TGGTGGACGT CGAATCGAGA AACAGTATGG AAAGCATTAA TATGTCATGC     480

ACCAAAAGAA GCTAATTATT TTATAAAAAC AGCGTGTAAT GTAGGAAAAG GAACTAATGG     540

TCAATGCCAT TGCATTGGTG GAGATGTTCC CACATATTTC GATTATGTGC CGCAGTATCT     600

TCGCTGGTTC GAGGAATGGG CAGAAGACTT TTGCAGGAAA AAAAAAAAAA AACTAGAAAA     660

TTTGCAAAAA CAGTGTCGTG ATTACGAACA AAATTTATAT TGTAGTGGTA ATGGCTACGA     720

TTGCACAAAA ACTATATATA AAAAAGGTAA ACTTGTTATA GGTGAACATT GTACAAACTG     780

TTCTGTTTGG TGTCGTATGT ATGAAACTTG GATAGATAAC CAGAAAAAAG AATTTCTAAA     840

ACAAAAAAGA AAATACGAAA CAGAAATATC AGGTGGTGGT AGTGGTAAGA GTCCTAAAAG     900

GACAAAACGG GCTGCACGTA GTAGTAGTAG TAGTGATGAT AATGGGTATG AAAGTAAATT     960

TTATAAAAAA CTGAAAGAAG TTGGCTACCA AGATGTCGAA AAATTTTTAA AAATATTAAA    1020

CAAAGAAGGA ATATGTCAAA ACAACCTCA AGTAGGAAAT GAAAAAGCAG ATAATGTTGA     1080

TTTTACTAAT GAAAAATATG TAAAAACATT TTCTCGTACA GAAATTTGTG AACCGTGCCC    1140

ATGGTGTGGA TTGGAAAAAG GTGGTCCACC ATGGAAAGTT AAAGGTGACA AAACCTGCGG    1200

AAGTGCAAAA ACAAAGACAT ACGATCCTAA AATATTACC GATATACCAG TACTCTACCC     1260

TGATAAATCA CAGCAAAATA TACTAAAAAA ATATAAAAAT TTTTGTGAAA AAGGTGCACC    1320

TGGTGGTGGT CAAATTAAAA AATGGCAATG TTATTATGAT GAACATAGGC CTAGTAGTAA    1380

AAATAATAAT AATTGTGTAG AAGGAACATG GGACAAGTTT ACACAAGGTA AACAAACCGT    1440

TAAGTCCTAT AATGTTTTTT TTGGGATTG GGTTCGATG ATGTTACACG ATTCTGTAGA     1500

GTGGAAGACA GAACTTAGTA AGTGTATAAA TAATAACACT AATGGCAACA CATGTAGAAA    1560

CAATAATAAA TGTAAAACAG ATTGTGGTTG TTTTCAAAAA TGGGTTGAAA AAAACAACA     1620

AGAATGGATG GCAATAAAAG ACCATTTTGG AAAGCAAACA GATATTGTCC AACAAAAAGG    1680

TCTTATCGTA TTTAGTCCCT ATGGAGTTCT TGACCTTGTT TTGAAGGGCG GTAATCTGTT    1740

GCAAAATATT AAAGATGTTC ATGGAGATAC AGATGACATA AACACATTA AGAAACTGTT     1800
```

-continued

```
GGATGAGGAA GACGCAGTAG CAGTTGTTCT TGGTGGCAAG GACAATACCA CAATTGATAA    1860

ATTACTACAA CACGAAAAAG AACAAGCAGA ACAATGCAAA CAAAAGCAGG AAGAATGCGA    1920

GAAAAAAGCA CAACAAGAAA GTCGTGGTCG CTCCGCCGAA ACCCGCGAAG ACGAAAGGAC    1980

ACAACAACCT GCTGATAGTG CCGGCGAAGT CGAAGAAGAA GAAGACGACG ACGACTACGA    2040

CGAAGACGAC GAAGATGACG ACGTAGTCCA GGACGTAGAT GTAAGTGAAA TAAGAGGTCC    2100

G                                                                  2101
```

(2) INFORMATION FOR SEQ ID NO: 10:

(i) SEQUENCE CHARACTERISTICS:
  (A) LENGTH: 700 amino acids
  (B) TYPE: amino acid
  (C) STRANDEDNESS: single
  (D) TOPOLOGY: linear (ii) MOLECULE TYPE: protein (iii) HYPOTHETICAL: NO (vi) ORIGINAL SOURCE:
  (A) ORGANISM: Plasmodium falciparum (xi) SEQUENCE DESCRIPTION: SEQ ID NO: 10:

```
Glu Gln Gly Asp Asn Lys Val Gly Ala Cys Ala Pro Tyr Arg Arg Leu
1               5                   10                  15

His Leu Cys Asp Tyr Asn Leu Glu Ser Ile Asp Thr Thr Ser Thr Thr
            20                  25                  30

His Lys Leu Leu Leu Glu Val Cys Met Ala Ala Lys Tyr Glu Gly Asn
        35                  40                  45

Ser Ile Asn Thr His Tyr Thr Gln His Gln Arg Thr Asn Glu Asp Ser
    50                  55                  60

Ala Ser Gln Leu Cys Thr Val Leu Ala Arg Ser Phe Ala Asp Ile Gly
65                  70                  75                  80

Asp Ile Val Arg Gly Lys Asp Leu Tyr Leu Gly Tyr Asp Asn Lys Glu
                85                  90                  95

Lys Glu Gln Arg Lys Lys Leu Glu Gln Lys Leu Lys Asp Ile Phe Lys
            100                 105                 110

Lys Ile His Lys Asp Val Met Lys Thr Asn Gly Ala Gln Glu Arg Tyr
        115                 120                 125

Ile Asp Asp Ala Lys Gly Gly Asp Phe Phe Gln Leu Arg Glu Asp Trp
    130                 135                 140

Trp Thr Ser Asn Arg Glu Thr Val Trp Lys Ala Leu Ile Cys His Ala
145                 150                 155                 160

Pro Lys Glu Ala Asn Tyr Phe Ile Lys Thr Ala Cys Asn Val Gly Lys
                165                 170                 175

Gly Thr Asn Gly Gln Cys His Cys Ile Gly Gly Asp Val Pro Thr Tyr
            180                 185                 190

Phe Asp Tyr Val Pro Gln Tyr Leu Arg Trp Phe Glu Glu Trp Ala Glu
        195                 200                 205

Asp Phe Cys Arg Lys Lys Lys Lys Leu Glu Asn Leu Gln Lys Gln
    210                 215                 220

Cys Arg Asp Tyr Glu Gln Asn Leu Tyr Cys Ser Gly Asn Gly Tyr Asp
225                 230                 235                 240

Cys Thr Lys Thr Ile Tyr Lys Lys Gly Lys Leu Val Ile Gly Glu His
                245                 250                 255

Cys Thr Asn Cys Ser Val Trp Cys Arg Met Tyr Glu Thr Trp Ile Asp
```

-continued

```
                    260                 265                 270
Asn Gln Lys Lys Glu Phe Leu Lys Gln Lys Arg Lys Tyr Glu Thr Glu
                275                 280                 285
Ile Ser Gly Gly Gly Ser Gly Lys Ser Pro Lys Arg Thr Lys Arg Ala
            290                 295                 300
Ala Arg Ser Ser Ser Ser Asp Asp Asn Gly Tyr Glu Ser Lys Phe
305                 310                 315                 320
Tyr Lys Lys Leu Lys Glu Val Gly Tyr Gln Asp Val Asp Lys Phe Leu
                325                 330                 335
Lys Ile Leu Asn Lys Glu Gly Ile Cys Gln Lys Gln Pro Gln Val Gly
                340                 345                 350
Asn Glu Lys Ala Asp Asn Val Asp Phe Thr Asn Glu Lys Tyr Val Lys
                355                 360                 365
Thr Phe Ser Arg Thr Glu Ile Cys Glu Pro Cys Pro Trp Cys Gly Leu
            370                 375                 380
Glu Lys Gly Gly Pro Pro Trp Lys Val Lys Gly Asp Lys Thr Cys Gly
385                 390                 395                 400
Ser Ala Lys Thr Lys Thr Tyr Asp Pro Lys Asn Ile Thr Asp Ile Pro
                405                 410                 415
Val Leu Tyr Pro Asp Lys Ser Gln Gln Asn Ile Leu Lys Lys Tyr Lys
                420                 425                 430
Asn Phe Cys Glu Lys Gly Ala Pro Gly Gly Gly Gln Ile Lys Lys Trp
            435                 440                 445
Gln Cys Tyr Tyr Asp Glu His Arg Pro Ser Ser Lys Asn Asn Asn Asn
        450                 455                 460
Cys Val Glu Gly Thr Trp Asp Lys Phe Thr Gln Gly Lys Gln Thr Val
465                 470                 475                 480
Lys Ser Tyr Asn Val Phe Phe Trp Asp Trp Val His Asp Met Leu His
                485                 490                 495
Asp Ser Val Glu Trp Lys Thr Glu Leu Ser Lys Cys Ile Asn Asn Asn
            500                 505                 510
Thr Asn Gly Asn Thr Cys Arg Asn Asn Asn Lys Cys Lys Thr Asp Cys
        515                 520                 525
Gly Cys Phe Gln Lys Trp Val Glu Lys Gln Gln Glu Trp Met Ala
530                 535                 540
Ile Lys Asp His Phe Gly Lys Gln Thr Asp Ile Val Gln Gln Lys Gly
545                 550                 555                 560
Leu Ile Val Phe Ser Pro Tyr Gly Val Leu Asp Leu Val Leu Lys Gly
                565                 570                 575
Gly Asn Leu Leu Gln Asn Ile Lys Asp Val His Gly Asp Thr Asp Asp
            580                 585                 590
Ile Lys His Ile Lys Lys Leu Leu Asp Glu Glu Asp Ala Val Ala Val
        595                 600                 605
Val Leu Gly Gly Lys Asp Asn Thr Thr Ile Asp Lys Leu Leu Gln His
            610                 615                 620
Glu Lys Glu Gln Ala Glu Gln Cys Lys Gln Lys Gln Glu Glu Cys Glu
625                 630                 635                 640
Lys Lys Ala Gln Gln Glu Ser Arg Gly Arg Ser Ala Glu Thr Arg Glu
                645                 650                 655
Asp Glu Arg Thr Gln Gln Pro Ala Asp Ser Ala Gly Glu Val Glu
            660                 665                 670
Glu Glu Asp Asp Asp Asp Tyr Asp Glu Asp Asp Glu Asp Asp Val
                675                 680                 685
```

```
    Val Gln Asp Val Asp Val Ser Glu Ile Arg Gly Pro
     690                 695                 700

(2) INFORMATION FOR SEQ ID NO: 11:

(i) SEQUENCE CHARACTERISTICS:
        (A) LENGTH: 8220 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO: 11:

AAAAATGGGG CCCAAGGAGG CTGCAGGTGG GGATGATATT GAGGATGAAA GTGCCAAACA      60

TATGTTTGAT AGGATAGGAA AAGATGTGTA CGATAAAGTA AAAGAGGAAG CTAAAGAACG     120

TGGTAAAGGC TTGCAAGGAC GTTTGTCAGA AGCAAAATTT GAGAAAAATG AAAGCGATCC     180

ACAAACACCA GAAGATCCAT GCGATCTTGA TCATAAATAT CATACAAATG TAACTACTAA     240

TGTAATTAAT CCGTGCGCTG ATAGATCTGA CGTGCGTTTT TCCGATGAAT ATGGAGGTCA     300

ATGTACACAT AATAGAATAA AAGATAGTCA ACAGGGTGAT AATAAAGGTG CATGTGCTCC     360

ATATAGGCGA TTGCATGTAT GCGATCAAAA TTTAGAACAG ATAGAGCCTA TAAAAATAAC     420

AAATACTCAT AATTTATTGG TAGATGTGTG TATGGCAGCA AAATTTGAAG ACAATCAAT     480

AACACAAGAT TATCCAAAAT ATCAAGCAAC ATATGGTGAT TCTCCTTCTC AAATATGTAC     540

TATGCTGGCA CGAAGTTTTG CGGACATAGG GGACATTGTC AGAGGAAGAG ATTTGTATTT     600

AGGTAATCCA CAAGAAATAA AACAAAGACA ACAATTAGAA AATAATTTGA AAACAATTTT     660

CGGGAAAATA TATGAAAAAT TGAATGGCGC AGAAGCACGC TACGGAAATG ATCCGGAATT     720

TTTTAAATTA CGAGAAGATT GGTGGACTGC TAATCGAGAA ACAGTATGGA AAGCCATCAC     780

ATGTAACGCT TGGGGTAATA CATATTTTCA TGCAACGTGC AATAGAGGAG AACGAACTAA     840

AGGTTACTGC CGGTGTAACG ACGACCAAGT TCCCACATAT TTTGATTATG TGCCGCAGTA     900

TCTTCGCTGG TTCGAGGAAT GGGCAGAAGA TTTTTGTAGG AAAAAAAATA AAAAAATAAA     960

AGATGTTAAA AGAAATTGTC GTGGAAAAGA TAAAGAGGAT AAGGATCGAT ATTGTAGCCG    1020

TAATGGCTAC GATTGCGAAA AAACTAAACG AGCGATTGGT AAGTTGCGTT ATGGTAAGCA    1080

ATGCATTAGC TGTTTGTATG CATGTAATCC TTACGTTGAT TGGATAAATA CCAAAAAGA    1140

ACAATTTGAC AAACAGAAAA AAAAATATGA TGAAGAAATA AAAAAATATG AAAATGGAGC    1200

ATCAGGTGGT AGTAGGCAAA AACGGGATGC AGGTGGTACA ACTACTACTA ATTATGATGG    1260

ATATGAAAAA AAATTTTATG ACGAACTTAA TAAAAGTGAA TATAGAACCG TTGATAAATT    1320

TTTGGAAAAA TTAAGTAATG AAGAAATATG CACAAAAGTT AAAGACGAAG AAGGAGGAAC    1380

AATTGATTTT AAAAACGTTA ATAGTGATAG TACTAGTGGT GCTAGTGGCA CTAATGTTGA    1440

AAGTCAAGGA ACATTTTATC GTTCAAAATA TTGCCAACCC TGCCCTTATT GTGGAGTGAA    1500

AAAGGTAAAT AATGGTGGTA GTAGTAATGA ATGGGAAGAG AAAAATAATG GCAAGTGCAA    1560

GAGTGGAAAA CTTTATGAGC CTAAACCCGA CAAAGAAGGT ACTACTATTA CAATCCTTAA    1620

AAGTGGTAAA GGACATGATG ATATTGAAGA AAAATTAAAC AAATTTTGTG ATGAAAAAAA    1680

TGGTGATACA ATAAATAGTG GTGGTAGTGG TACGGGTGGT AGTGGTGGTG GTAACAGTGG    1740
```

```
TAGACAGGAA TTGTATGAAG AATGGAAATG TTATAAAGGT GAAGATGTAG TGAAAGTTGG    1800

ACACGATGAG GATGACGAGG AGGATTATGA AAATGTAAAA AATGCAGGCG GATTATGTAT    1860

ATTAAAAAAC CAAAAAAAGA ATAAAGAAGA AGGTGGAAAT ACGTCTGAAA AGGAGCCTGA    1920

TGAAATCCAA AAGACATTCA ATCCTTTTTT TTACTATTGG GTTGCACATA TGTTAAAAGA    1980

TTCCATACAT TGGAAAAAAA AACTTCAGAG ATGTTTACAA AATGGTAACA GAATAAAATG    2040

TGGAAACAAT AAATGTAATA ATGATTGTGA ATGTTTTAAA AGATGGATTA CACAAAAAAA    2100

AGACGAATGG GGGAAAATAG TACAACATTT TAAAACGCAA AATATTAAAG GTAGAGGAGG    2160

TAGTGACAAT ACGGCAGAAT TAATCCCATT TGATCACGAT TATGTTCTTC AATACAATTT    2220

GCAAGAAGAA TTTTTGAAAG GCGATTCCGA AGACGCTTCC GAAGAAAAAT CCGAAAATAG    2280

TCTGGATGCA GAGGAGGCAG AGGAACTAAA ACACCTTCGC GAAATCATTG AAAGTGAAGA    2340

CAATAATCAA GAAGCATCTG TTGGTGGTGG CGTCACTGAA CAAAAAAATA TAATGGATAA    2400

ATTGCTCAAC TACGAAAAAG ACGAAGCCGA TTTATGCCTA GAAATTCACG AAGATGAGGA    2460

AGAGGAAAAA GAAAAAGGAG ACGGAAACGA ATGTATCGAA GAGGGCGAAA ATTTTCGTTA    2520

TAATCCATGT AGTGGCGAAA GTGGTAACAA ACGATACCCC GTTCTTGCGA ACAAAGTAGC    2580

GTATCAAATG CATCACAAGG CAAAGACACA ATTGGCTAGT CGTGCTGGTA GAAGTGCGTT    2640

GAGAGGTGAT ATATCCTTAG CGCAATTTAA AAATGGTCGT AACGGAAGTA CATTGAAAGG    2700

ACAAATTTGC AAAATTAACG AAAACTATTC CAATGATAGT CGTGGTAATA GTGGTGGACC    2760

ATGTACAGGC AAAGATGGAG ATCACGGAGG TGTGCGCATG AGAATAGGAA CGGAATGGTC    2820

AAATATTGAA GGAAAAAAAC AAACGTCATA CAAAAACGTC TTTTTACCTC CCCGACGAGA    2880

ACACATGTGT ACATCCAATT TAGAAAATTT AGATGTTGGT AGTGTCACTA AAAATGATAA    2940

GGCTAGCCAC TCATTATTGG GAGATGTTCA GCTCGCAGCA AAAACTGATG CAGCTGAGAT    3000

AATAAAACGC TATAAAGATC AAAATAATAT ACAACTAACT GATCCAATAC AACAAAAAGA    3060

CCAGGAGGCT ATGTGTCGAG CTGTACGTTA TAGTTTTGCC GATTTAGGAG ACATTATTCG    3120

AGGAAGAGAT ATGTGGGATG AGGATAAGAG CTCAACAGAC ATGGAAACAC GTTTGATAAC    3180

CGTATTTAAA AACATTAAAG AAAAACATGA TGGAATCAAA GACAACCCTA AATATACCGG    3240

TGATGAAAGC AAAAAGCCCG CATATAAAAA ATTACGAGCA GATTGGTGGG AAGCAAATAG    3300

ACATCAAGTG TGGAGAGCCA TGAAATGCGC AACAAAAGGC ATCATATGTC CTGGTATGCC    3360

AGTTGACGAT TATATCCCCC AACGTTTACG CTGGATGACT GAATGGGCTG AATGGTATTG    3420

TAAAGCGCAA TCACAGGAGT ATGACAAGTT AAAAAAAATC TGTGCAGATT GTATGAGTAA    3480

GGGTGATGGA AAATGTACGC AAGGTGATGT CGATTGTGGA AAGTGCAAAG CAGCATGTGA    3540

TAAATATAAA GAGGAAATAG AAAAATGGAA TGAACAATGG AGAAAAATAT CAGATAAATA    3600

CAATCTATTA TACCTACAAG CAAAAACTAC TTCTACTAAT CCTGGCCGTA CTGTTCTTGG    3660

TGATGACGAT CCCGACTATC AACAAATGGT AGATTTTTTG ACCCCAATAC ACAAAGCAAG    3720

TATTGCCGCA CGTGTTCTTG TTAAACGTGC TGCTGGTAGT CCCACTGAGA TCGCCGCCGC    3780

CGCCCCGATC ACCCCCTACA GTACTGCTGC CGGATATATA CACCAGGAAA TAGGATATGG    3840

GGGGTGCCAG GAACAACAC AATTTTGTGA AAAAAAACAT GGTGCAACAT CAACTAGTAC    3900

CACGAAAGAA AACAAAGAAT ACACCTTTAA ACAACCTCCG CCGGAGTATG CTACAGCGTG    3960

TGATTGCATA AATAGGTCGC AAACAGAGGA GCCGAAGAAA AAGGAAGAAA ATGTAGAGAG    4020

TGCCTGCAAA ATAGTGGAGA AAATACTTGA GGGTAAGAAT GGAAGGACTA CAGTAGGTGA    4080
```

-continued

| | | | | | |
|---|---|---|---|---|---|
| ATGTAATCCA | AAAGAGAGTT | ATCCTGATTG | GGATTGCAAA | AACAATATTG | ACATTAGTCA | 4140 |
| TGATGGTGCT | TGTATGCCTC | CAAGGAGACA | AAAACTATGT | TTATATTATA | TAGCACATGA | 4200 |
| GAGTCAAACA | GAAAATATAA | AAACAGACGA | TAATTTGAAA | GATGCTTTTA | TTAAAACTGC | 4260 |
| AGCAGCAGAA | ACTTTTCTTT | CATGGCAATA | TTATAAGAGT | AAGAATGATA | GTGAAGCTAA | 4320 |
| AATATTAGAT | AGAGGCCTTA | TTCCATCCCA | ATTTTTAAGA | TCCATGATGT | ACACGTTTGG | 4380 |
| AGATTATAGA | GATATATGTT | TGAACACAGA | TATATCTAAA | AACAAAATG | ATGTAGCTAA | 4440 |
| GGCAAAAGAT | AAAATAGGTA | AATTTTTCTC | AAAAGATGGC | AGCAAATCTC | CTAGTGGCTT | 4500 |
| ATCACGCCAA | GAATGGTGGA | AAACAAATGG | TCCAGAGATT | TGGAAAGGAA | TGTTATGTGC | 4560 |
| CTTAACAAAA | TACGTCACAG | ATACCGATAA | CAAAAGAAAA | ATCAAAAACG | ACTACTCATA | 4620 |
| CGATAAAGTC | AACCAATCCC | AAAATGGCAA | CCCTTCCCTT | GAAGAGTTTG | CTGCTAAACC | 4680 |
| TCAATTTCTA | CGTTGGATGA | TCGAATGGGG | AGAAGAGTTT | TGTGCTGAAC | GTCAGAAGAA | 4740 |
| GGAAAATATC | ATAAAAGATG | CATGTAATGA | AATAAATTCT | ACACAACAGT | GTAATGATGC | 4800 |
| GAAACATCGT | TGTAATCAAG | CATGTAGAGC | ATATCAAGAA | TATGTTGAAA | ATAAAAAAAA | 4860 |
| AGAATTTTCG | GGACAAACAA | ATAACTTTGT | TCTAAAGGCA | AATGTTCAGC | CCAAGATCC | 4920 |
| AGAATATAAA | GGATATGAAT | ATAAAGACGG | CGTACAACCG | ATACAGGGGA | ATGAGTATTT | 4980 |
| ACTGCAAAAA | TGTGATAATA | ATAAATGTTC | TTGCATGGAT | GGAAATGTAC | TTTCCGTCTC | 5040 |
| TCCAAAAGAA | AAACCTTTTG | GAAAATATGC | CCATAAATAT | CCTGAGAAAT | GTGATTGTTA | 5100 |
| TCAAGGAAAA | CATGTACCTA | GCATACCACC | TCCCCCCCCA | CCTGTACAAC | CACAACCGGA | 5160 |
| AGCACCAACA | GTAACAGTAG | ACGTTTGCAG | CATAGTAAAA | ACACTATTTA | AAGACACAAA | 5220 |
| CAATTTTTCC | GACGCTTGTG | GTCTAAAATA | CGGCAAAACC | GCACCATCCA | GTTGGAAATG | 5280 |
| TATACCAAGT | GACACAAAAA | GTGGTGCTGG | TGCCACCACC | GGCAAAAGTG | GTAGTGATAG | 5340 |
| TGGTAGTATT | TGTATCCCAC | CCAGGAGGCG | ACGATTATAT | GTGGGAAAC | TACAGGAGTG | 5400 |
| GGCTACCGCG | CTCCCACAAG | GTGAGGGCGC | CGCGCCGTCC | CACTCACGCG | CCGACGACTT | 5460 |
| GCGCAATGCG | TTCATCCAAT | CTGCTGCAAT | AGAGACTTTT | TTCTTATGGG | ATAGATATAA | 5520 |
| AGAAGAGAAA | AAACCACAGG | GTGATGGGTC | ACAACAAGCA | CTATCACAAC | TAACCAGTAC | 5580 |
| ATACAGTGAT | GACGAGGAGG | ACCCCCCCGA | CAAACTGTTA | CAAAATGGTA | AGATACCCCC | 5640 |
| CGATTTTTTG | AGATTAATGT | TCTATACATT | AGGAGATTAT | AGGGATATTT | TAGTACACGG | 5700 |
| TGGTAACACA | AGTGACAGTG | GTAACACAAA | TGGTAGTAAC | AACAACAATA | TTGTGCTTGA | 5760 |
| AGCGAGTGGT | AACAAGGAGG | ACATGCAAAA | AATACAAGAG | AAAATAGAAC | AAATTCTCCC | 5820 |
| AAAAAATGGT | GGCACACCTC | TTGTCCCAAA | ATCTAGTGCC | CAAACACCTG | ATAAATGGTG | 5880 |
| GAATGAACAC | GCCGAATCTA | TCTGGAAAGG | TATGATATGT | GCATTGACAT | ATACAGAAAA | 5940 |
| GAACCCTGAC | ACCAGTGCAA | GAGGCGACGA | AAACAAAATA | GAAAGGATG | ATGAAGTGTA | 6000 |
| CGAGAAATTT | TTTGGCAGCA | CAGCCGACAA | ACATGGCACA | GCCTCAACCC | CAACCGGCAC | 6060 |
| ATACAAAACC | CAATACGACT | ACGAAAAAGT | CAAACTTGAG | GATACAAGTG | GTGCCAAAAC | 6120 |
| CCCCTCAGCC | TCTAGTGATA | CACCCCTTCT | CTCCGATTTC | GTGTTACGCC | CCCCCTACTT | 6180 |
| CCGTTACCTT | GAAGAATGGG | GTCAAAATTT | TTGTAAAAAA | AGAAAGCATA | AATTGGCACA | 6240 |
| AATAAAACAT | GAGTGTAAAG | TAGAAGAAAA | TGGTGGTGGT | AGTCGTCGTG | GTGGTATAAC | 6300 |
| AAGACAATAT | AGTGGGGATG | GCGAAGCGTG | TAATGAGATG | CTTCCAAAAA | ACGATGGAAC | 6360 |
| TGTTCCGGAT | TTAGAAAAGC | CGAGTTGTGC | CAAACCTTGT | AGTTCTTATA | GAAAATGGAT | 6420 |
| AGAAAGCAAG | GGAAAAGAGT | TTGAGAAACA | AGAAAAGGCA | TATGAACAAC | AAAAAGACAA | 6480 |

```
ATGTGTAAAT GGAAGTAATA AGCATGATAA TGGATTTTGT GAAACACTAA CAACGTCCTC    6540

TAAAGCTAAA GACTTTTTAA AAACGTTAGG ACCATGTAAA CCTAATAATG TAGAGGGTAA    6600

AACAATTTTT GATGATGATA AAACCTTTAA ACATACAAAA GATTGTGATC CATGTCTTAA    6660

ATTTAGTGTT AATTGTAAAA AAGATGAATG TGATAATTCT AAAGGAACCG ATTGCCGAAA    6720

TAAAAATAGT ATTGATGCAA CAGATATTGA AAATGGAGTG GATTCTACTG TACTAGAAAT    6780

GCGTGTCAGT GCTGATAGTA AAAGTGGATT TAATGGTGAT GGTTTAGAGA ATGCTTGTAG    6840

AGGTGCTGGT ATCTTTGAAG GTATTAGAAA AGATGAATGG AAATGTCGTA ATGTATGTGG    6900

TTATGTTGTA TGTAAACCGG AAAACGTTAA TGGGGAAGCA AAGGGAAAAC ACATTATACA    6960

AATTAGAGCA CTGGTTAAAC GTTGGGTAGA ATATTTTTTT GAAGATTATA ATAAAATAAA    7020

ACATAAAATT TCACATCGCA TAAAAAATGG TGAAATATCT CCATGTATAA AAAATTGTGT    7080

AGAAAAATGG GTAGATCAGA AAAGAAAAGA ATGGAAGGAA ATTACTGAAC GTTTCAAAGA    7140

TCAATATAAA AATGACAATT CAGATGATGA CAATGTGAGA AGTTTTTTGG AGACCTTGAT    7200

ACCTCAAATT ACTGATGCAA ACGCTAAAAA TAAGGTTATA AAATTAAGTA AGTTCGGTAA    7260

TTCTTGTGGA TGTAGTGCCA GTGCGAACGA ACAAAACAAA AATGGTGAAT ACAAGGACGC    7320

TATAGATTGT ATGCTTAAAA AGCTTAAAGA TAAAATTGGC GAGTGCGAAA AGAAACACCA    7380

TCAAACTAGT GATACCGAGT GTTCCGACAC ACCACAACCG CAAACCCTTG AAGACGAAAC    7440

TTTGGATGAT GATATAGAAA CAGAGGAGGC GAAGAAGAAC ATGATGCCGA AAATTTGTGA    7500

AAATGTGTTA AAAACAGCAC AACAAGAGGA TGAAGGCGGT TGTGTCCCAG CAGAAAATAG    7560

TGAAGAACCG GCAGCAACAG ATAGTGGTAA GGAAACCCCC GAACAAACCC CCGTTCTCAA    7620

ACCCGAAGAA GAAGCAGTAC CGGAACCACC ACCTCCACCC CCACAGGAAA AGCCCCGGC    7680

ACCAATACCC CAACCACAAC CACCAACCCC CCCCACACAA CTCTTGGATA ATCCCCACGT    7740

TCTAACCGCC CTGGTGACCT CCACCCTCGC CTGGAGCGTT GGCATCGGTT TTGCTACATT    7800

CACTTATTTT TATCTAAAGG TAAATGGAAG TATATATATG GGGATGTGGA TGTATGTGGA    7860

TGTATGTGAA TGTATGTGGA TGTATGTGGA TGTATGTGGA TGTGTTTTAT GGATATGTAT    7920

TTGTGATTAT GTTTGGATAT ATATATATAT ATATATATGT TTATGTATAT GTGTTTTTGG    7980

ATATATATAT GTGTATGTAT ATGATTTTCT GTATATGTAT TTGTGGGTTA AGGATATATA    8040

TATATGGATG TACTTGTATG TGTTTTATAT ATATATTTTA TATATATGTA TTTATATTAA    8100

AAAAGAAATA TAAAAACAAA TTTATTAAAA TGAAAAAAAG AAAAATGAAA TATAAAAAAA    8160

AATTTATTAA AATAAAAAAA AAAAAAAAAA AAAAGGAGAA AAATTTTTTA AAAAATAATA    8220
```

(2) INFORMATION FOR SEQ ID NO: 12:

(i) SEQUENCE CHARACTERISTICS:
        (A) LENGTH: 2710 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO: 12:

```
Asn Val Met Val Glu Leu Ala Lys Met Gly Pro Lys Glu Ala Ala Gly
1               5                  10                  15
```

```
Gly Asp Asp Ile Glu Asp Glu Ser Ala Lys His Met Phe Asp Arg Ile
         20                  25                  30
Gly Lys Asp Val Tyr Asp Lys Val Lys Glu Glu Ala Lys Glu Arg Gly
         35                  40                  45
Lys Gly Leu Gln Gly Arg Leu Ser Glu Ala Lys Phe Glu Lys Asn Glu
 50                  55                  60
Ser Asp Pro Gln Thr Pro Glu Asp Pro Cys Asp Leu Asp His Lys Tyr
 65                  70                  75                  80
His Thr Asn Val Thr Thr Asn Val Ile Asn Pro Cys Ala Asp Arg Ser
             85                  90                  95
Asp Val Arg Phe Ser Asp Glu Tyr Gly Gly Gln Cys Thr His Asn Arg
             100                 105                 110
Ile Lys Asp Ser Gln Gln Gly Asp Asn Lys Gly Ala Cys Ala Pro Tyr
             115                 120                 125
Arg Arg Leu His Val Cys Asp Gln Asn Leu Glu Gln Ile Glu Pro Ile
 130                 135                 140
Lys Ile Thr Asn Thr His Asn Leu Leu Val Asp Val Cys Met Ala Ala
145                 150                 155                 160
Lys Phe Glu Gly Gln Ser Ile Thr Gln Asp Tyr Pro Lys Tyr Gln Ala
             165                 170                 175
Thr Tyr Gly Asp Ser Pro Ser Gln Ile Cys Thr Met Leu Ala Arg Ser
             180                 185                 190
Phe Ala Asp Ile Gly Asp Ile Val Arg Gly Arg Asp Leu Tyr Leu Gly
             195                 200                 205
Asn Pro Gln Glu Ile Lys Gln Arg Gln Gln Leu Glu Asn Asn Leu Lys
 210                 215                 220
Thr Ile Phe Gly Lys Ile Tyr Glu Lys Leu Asn Gly Ala Glu Ala Arg
225                 230                 235                 240
Tyr Gly Asn Asp Pro Glu Phe Phe Lys Leu Arg Glu Asp Trp Trp Thr
             245                 250                 255
Ala Asn Arg Glu Thr Val Trp Lys Ala Ile Thr Cys Asn Ala Trp Gly
             260                 265                 270
Asn Thr Tyr Phe His Ala Thr Cys Asn Arg Gly Glu Arg Thr Lys Gly
         275                 280                 285
Tyr Cys Arg Cys Asn Asp Asp Gln Val Pro Thr Tyr Phe Asp Tyr Val
         290                 295                 300
Pro Gln Tyr Leu Arg Trp Phe Glu Glu Trp Ala Glu Asp Phe Cys Arg
305                 310                 315                 320
Lys Lys Asn Lys Lys Ile Lys Asp Val Lys Arg Asn Cys Arg Gly Lys
                 325                 330                 335
Asp Lys Glu Asp Lys Asp Arg Tyr Cys Ser Arg Asn Gly Tyr Asp Cys
             340                 345                 350
Glu Lys Thr Lys Arg Ala Ile Gly Lys Leu Arg Tyr Gly Lys Gln Cys
         355                 360                 365
Ile Ser Cys Leu Tyr Ala Cys Asn Pro Tyr Val Asp Trp Ile Asn Asn
370                 375                 380
Gln Lys Glu Gln Phe Asp Lys Gln Lys Lys Tyr Asp Glu Glu Ile
385                 390                 395                 400
Lys Lys Tyr Glu Asn Gly Ala Ser Gly Gly Ser Arg Gln Lys Arg Asp
                 405                 410                 415
Ala Gly Gly Thr Thr Thr Thr Asn Tyr Asp Gly Tyr Glu Lys Lys Phe
             420                 425                 430
```

-continued

```
Tyr Asp Glu Leu Asn Lys Ser Glu Tyr Arg Thr Val Asp Lys Phe Leu
        435                 440                 445
Glu Lys Leu Ser Asn Glu Glu Ile Cys Thr Lys Val Lys Asp Glu Glu
    450                 455                 460
Gly Gly Thr Ile Asp Phe Lys Asn Val Asn Ser Asp Ser Thr Ser Gly
465                 470                 475                 480
Ala Ser Gly Thr Asn Val Glu Ser Gln Gly Thr Phe Tyr Arg Ser Lys
                485                 490                 495
Tyr Cys Gln Pro Cys Pro Tyr Cys Gly Val Lys Lys Val Asn Asn Gly
            500                 505                 510
Gly Ser Ser Asn Glu Trp Glu Lys Asn Asn Gly Lys Cys Lys Ser
        515                 520                 525
Gly Lys Leu Tyr Glu Pro Lys Pro Asp Lys Glu Gly Thr Thr Ile Thr
    530                 535                 540
Ile Leu Lys Ser Gly Lys Gly His Asp Asp Ile Glu Glu Lys Leu Asn
545                 550                 555                 560
Lys Phe Cys Asp Glu Lys Asn Gly Asp Thr Ile Asn Ser Gly Gly Ser
                565                 570                 575
Gly Thr Gly Gly Ser Gly Gly Asn Ser Gly Arg Gln Glu Leu Tyr
            580                 585                 590
Glu Glu Trp Lys Cys Tyr Lys Gly Glu Asp Val Val Lys Val Gly His
        595                 600                 605
Asp Glu Asp Asp Glu Glu Asp Tyr Glu Asn Val Lys Asn Ala Gly Gly
    610                 615                 620
Leu Cys Ile Leu Lys Asn Gln Lys Lys Asn Lys Glu Gly Gly Asn
625                 630                 635                 640
Thr Ser Glu Lys Glu Pro Asp Glu Ile Gln Lys Thr Phe Asn Pro Phe
                645                 650                 655
Phe Tyr Tyr Trp Val Ala His Met Leu Lys Asp Ser Ile His Trp Lys
            660                 665                 670
Lys Lys Leu Gln Arg Cys Leu Gln Asn Gly Asn Arg Ile Lys Cys Gly
        675                 680                 685
Asn Asn Lys Cys Asn Asn Asp Cys Glu Cys Phe Lys Arg Trp Ile Thr
    690                 695                 700
Gln Lys Lys Asp Glu Trp Gly Lys Ile Val Gln His Phe Lys Thr Gln
705                 710                 715                 720
Asn Ile Lys Gly Arg Gly Gly Ser Asp Asn Thr Ala Glu Leu Ile Pro
                725                 730                 735
Phe Asp His Asp Tyr Val Leu Gln Tyr Asn Leu Gln Glu Glu Phe Leu
            740                 745                 750
Lys Gly Asp Ser Glu Asp Ala Ser Glu Glu Lys Ser Glu Asn Ser Leu
        755                 760                 765
Asp Ala Glu Glu Ala Glu Glu Leu Lys His Leu Arg Glu Ile Ile Glu
    770                 775                 780
Ser Glu Asp Asn Asn Gln Glu Ala Ser Val Gly Gly Val Thr Glu
785                 790                 795                 800
Gln Lys Asn Ile Met Asp Lys Leu Leu Asn Tyr Glu Lys Asp Glu Ala
                805                 810                 815
Asp Leu Cys Leu Glu Ile His Glu Asp Glu Glu Glu Lys Glu Lys
            820                 825                 830
Gly Asp Gly Asn Glu Cys Ile Glu Glu Gly Glu Asn Phe Arg Tyr Asn
        835                 840                 845
Pro Cys Ser Gly Glu Ser Gly Asn Lys Arg Tyr Pro Val Leu Ala Asn
```

-continued

```
            850                 855                 860
Lys Val Ala Tyr Gln Met His His Lys Ala Lys Thr Gln Leu Ala Ser
865                 870                 875                 880
Arg Ala Gly Arg Ser Ala Leu Arg Gly Asp Ile Ser Leu Ala Gln Phe
                885                 890                 895
Lys Asn Gly Arg Asn Gly Ser Thr Leu Lys Gly Gln Ile Cys Lys Ile
            900                 905                 910
Asn Glu Asn Tyr Ser Asn Asp Ser Arg Gly Asn Ser Gly Gly Pro Cys
            915                 920                 925
Thr Gly Lys Asp Gly Asp His Gly Gly Val Arg Met Arg Ile Gly Thr
            930                 935                 940
Glu Trp Ser Asn Ile Glu Gly Lys Lys Gln Thr Ser Tyr Lys Asn Val
945                 950                 955                 960
Phe Leu Pro Pro Arg Arg Glu His Met Cys Thr Ser Asn Leu Glu Asn
                965                 970                 975
Leu Asp Val Gly Ser Val Thr Lys Asn Asp Lys Ala Ser His Ser Leu
            980                 985                 990
Leu Gly Asp Val Gln Leu Ala Ala Lys Thr Asp Ala Ala Glu Ile Ile
            995                 1000                1005
Lys Arg Tyr Lys Asp Gln Asn Asn Ile Gln Leu Thr Asp Pro Ile Gln
            1010                1015                1020
Gln Lys Asp Gln Glu Ala Met Cys Arg Ala Val Arg Tyr Ser Phe Ala
1025                1030                1035                1040
Asp Leu Gly Asp Ile Ile Arg Gly Arg Asp Met Trp Asp Glu Asp Lys
                1045                1050                1055
Ser Ser Thr Asp Met Glu Thr Arg Leu Ile Thr Val Phe Lys Asn Ile
                1060                1065                1070
Lys Glu Lys His Asp Gly Ile Lys Asp Asn Pro Lys Tyr Thr Gly Asp
            1075                1080                1085
Glu Ser Lys Lys Pro Ala Tyr Lys Lys Leu Arg Ala Asp Trp Trp Glu
            1090                1095                1100
Ala Asn Arg His Gln Val Trp Arg Ala Met Lys Cys Ala Thr Lys Gly
1105                1110                1115                1120
Ile Ile Cys Pro Gly Met Pro Val Asp Asp Tyr Ile Pro Gln Arg Leu
                1125                1130                1135
Arg Trp Met Thr Glu Trp Ala Glu Trp Tyr Cys Lys Ala Gln Ser Gln
                1140                1145                1150
Glu Tyr Asp Lys Leu Lys Lys Ile Cys Ala Asp Cys Met Ser Lys Gly
            1155                1160                1165
Asp Gly Lys Cys Thr Gln Gly Asp Val Asp Cys Gly Lys Cys Lys Ala
            1170                1175                1180
Ala Cys Asp Lys Tyr Lys Glu Glu Ile Glu Lys Trp Asn Glu Gln Trp
1185                1190                1195                1200
Arg Lys Ile Ser Asp Lys Tyr Asn Leu Leu Tyr Leu Gln Ala Lys Thr
                1205                1210                1215
Thr Ser Thr Asn Pro Gly Arg Thr Val Leu Gly Asp Asp Pro Asp
            1220                1225                1230
Tyr Gln Gln Met Val Asp Phe Leu Thr Pro Ile His Lys Ala Ser Ile
            1235                1240                1245
Ala Ala Arg Val Leu Val Lys Arg Ala Ala Gly Ser Pro Thr Glu Ile
            1250                1255                1260
Ala Ala Ala Ala Pro Ile Thr Pro Tyr Ser Thr Ala Ala Gly Tyr Ile
1265                1270                1275                1280
```

His Gln Glu Ile Gly Tyr Gly Gly Cys Gln Glu Gln Thr Gln Phe Cys
            1285                1290                1295

Glu Lys Lys His Gly Ala Thr Ser Thr Ser Thr Thr Lys Glu Asn Lys
        1300            1305                1310

Glu Tyr Thr Phe Lys Gln Pro Pro Glu Tyr Ala Thr Ala Cys Asp
        1315            1320            1325

Cys Ile Asn Arg Ser Gln Thr Glu Pro Lys Lys Glu Glu Asn
    1330            1335            1340

Val Glu Ser Ala Cys Lys Ile Val Glu Lys Ile Leu Glu Gly Lys Asn
1345            1350            1355            1360

Gly Arg Thr Thr Val Gly Glu Cys Asn Pro Lys Glu Ser Tyr Pro Asp
            1365            1370            1375

Trp Asp Cys Lys Asn Asn Ile Asp Ile Ser His Asp Gly Ala Cys Met
        1380            1385            1390

Pro Pro Arg Arg Gln Lys Leu Cys Leu Tyr Tyr Ile Ala His Glu Ser
        1395            1400            1405

Gln Thr Glu Asn Ile Lys Thr Asp Asp Asn Leu Lys Asp Ala Phe Ile
    1410            1415            1420

Lys Thr Ala Ala Ala Glu Thr Phe Leu Ser Trp Gln Tyr Tyr Lys Ser
1425            1430            1435            1440

Lys Asn Asp Ser Glu Ala Lys Ile Leu Asp Arg Gly Leu Ile Pro Ser
            1445            1450            1455

Gln Phe Leu Arg Ser Met Met Tyr Thr Phe Gly Asp Tyr Arg Asp Ile
        1460            1465            1470

Cys Leu Asn Thr Asp Ile Ser Lys Lys Gln Asn Asp Val Ala Lys Ala
        1475            1480            1485

Lys Asp Lys Ile Gly Lys Phe Phe Ser Lys Asp Gly Ser Lys Ser Pro
    1490            1495            1500

Ser Gly Leu Ser Arg Gln Glu Trp Trp Lys Thr Asn Gly Pro Glu Ile
1505            1510            1515            1520

Trp Lys Gly Met Leu Cys Ala Leu Thr Lys Tyr Val Thr Asp Thr Asp
            1525            1530            1535

Asn Lys Arg Lys Ile Lys Asn Asp Tyr Ser Tyr Asp Lys Val Asn Gln
        1540            1545            1550

Ser Gln Asn Gly Asn Pro Ser Leu Glu Glu Phe Ala Ala Lys Pro Gln
    1555            1560            1565

Phe Leu Arg Trp Met Ile Glu Trp Gly Glu Glu Phe Cys Ala Glu Arg
    1570            1575            1580

Gln Lys Lys Glu Asn Ile Ile Lys Asp Ala Cys Asn Glu Ile Asn Ser
1585            1590            1595            1600

Thr Gln Gln Cys Asn Asp Ala Lys His Arg Cys Asn Gln Ala Cys Arg
            1605            1610            1615

Ala Tyr Gln Glu Tyr Val Glu Asn Lys Lys Lys Glu Phe Ser Gly Gln
        1620            1625            1630

Thr Asn Asn Phe Val Leu Lys Ala Asn Val Gln Pro Gln Asp Pro Glu
    1635            1640            1645

Tyr Lys Gly Tyr Glu Tyr Lys Asp Gly Val Gln Pro Ile Gln Gly Asn
    1650            1655            1660

Glu Tyr Leu Leu Gln Lys Cys Asp Asn Asn Lys Cys Ser Cys Met Asp
1665            1670            1675            1680

Gly Asn Val Leu Ser Val Ser Pro Lys Glu Lys Pro Phe Gly Lys Tyr
            1685            1690            1695

-continued

Ala His Lys Tyr Pro Glu Lys Cys Asp Cys Tyr Gln Gly Lys His Val
        1700                1705                1710
Pro Ser Ile Pro Pro Pro Pro Val Gln Pro Gln Pro Glu Ala
        1715                1720            1725
Pro Thr Val Thr Val Asp Val Cys Ser Ile Val Lys Thr Leu Phe Lys
        1730                1735                1740
Asp Thr Asn Asn Phe Ser Asp Ala Cys Gly Leu Lys Tyr Gly Lys Thr
1745                1750                1755                1760
Ala Pro Ser Ser Trp Lys Cys Ile Pro Ser Asp Thr Lys Ser Gly Ala
            1765                1770                1775
Gly Ala Thr Thr Gly Lys Ser Gly Ser Asp Ser Gly Ser Ile Cys Ile
            1780                1785                1790
Pro Pro Arg Arg Arg Arg Leu Tyr Val Gly Lys Leu Gln Glu Trp Ala
            1795                1800                1805
Thr Ala Leu Pro Gln Gly Glu Gly Ala Ala Pro Ser His Ser Arg Ala
            1810                1815                1820
Asp Asp Leu Arg Asn Ala Phe Ile Gln Ser Ala Ala Ile Glu Thr Phe
1825                1830                1835                1840
Phe Leu Trp Asp Arg Tyr Lys Glu Glu Lys Pro Gln Gly Asp Gly
            1845                1850                1855
Ser Gln Gln Ala Leu Ser Gln Leu Thr Ser Thr Tyr Ser Asp Asp Glu
            1860                1865                1870
Glu Asp Pro Pro Asp Lys Leu Leu Gln Asn Gly Lys Ile Pro Pro Asp
            1875                1880                1885
Phe Leu Arg Leu Met Phe Tyr Thr Leu Gly Asp Tyr Arg Asp Ile Leu
            1890                1895                1900
Val His Gly Gly Asn Thr Ser Asp Ser Gly Asn Thr Asn Gly Ser Asn
1905                1910                1915                1920
Asn Asn Asn Ile Val Leu Glu Ala Ser Gly Asn Lys Glu Asp Met Gln
                1925                1930                1935
Lys Ile Gln Glu Lys Ile Glu Gln Ile Leu Pro Lys Asn Gly Gly Thr
                1940                1945                1950
Pro Leu Val Pro Lys Ser Ser Ala Gln Thr Pro Asp Lys Trp Trp Asn
            1955                1960                1965
Glu His Ala Glu Ser Ile Trp Lys Gly Met Ile Cys Ala Leu Thr Tyr
            1970                1975                1980
Thr Glu Lys Asn Pro Asp Thr Ser Ala Arg Gly Asp Glu Asn Lys Ile
1985                1990                1995                2000
Glu Lys Asp Asp Glu Val Tyr Glu Lys Phe Phe Gly Ser Thr Ala Asp
                2005                2010                2015
Lys His Gly Thr Ala Ser Thr Pro Thr Gly Thr Tyr Lys Thr Gln Tyr
            2020                2025                2030
Asp Tyr Glu Lys Val Lys Leu Glu Asp Thr Ser Gly Ala Lys Thr Pro
            2035                2040                2045
Ser Ala Ser Ser Asp Thr Pro Leu Leu Ser Asp Phe Val Leu Arg Pro
2050                2055                2060
Pro Tyr Phe Arg Tyr Leu Glu Glu Trp Gly Gln Asn Phe Cys Lys Lys
2065                2070                2075                2080
Arg Lys His Lys Leu Ala Gln Ile Lys His Glu Cys Lys Val Glu Glu
            2085                2090                2095
Asn Gly Gly Gly Ser Arg Arg Gly Gly Ile Thr Arg Gln Tyr Ser Gly
            2100                2105                2110
Asp Gly Glu Ala Cys Asn Glu Met Leu Pro Lys Asn Asp Gly Thr Val

```
                    2115                2120                2125
Pro Asp Leu Glu Lys Pro Ser Cys Ala Lys Pro Cys Ser Ser Tyr Arg
    2130                2135                2140
Lys Trp Ile Glu Ser Lys Gly Lys Glu Phe Glu Lys Gln Gln Lys Ala
2145                2150                2155                2160
Tyr Glu Gln Gln Lys Asp Lys Cys Val Asn Gly Ser Asn Lys His Asp
                2165                2170                2175
Asn Gly Phe Cys Glu Thr Leu Thr Thr Ser Lys Ala Lys Asp Phe
            2180                2185                2190
Leu Lys Thr Leu Gly Pro Cys Lys Pro Asn Asn Val Glu Gly Lys Thr
            2195                2200                2205
Ile Phe Asp Asp Lys Thr Phe Lys His Thr Lys Asp Cys Asp Pro
    2210                2215                2220
Cys Leu Lys Phe Ser Val Asn Cys Lys Lys Asp Glu Cys Asp Asn Ser
2225                2230                2235                2240
Lys Gly Thr Asp Cys Arg Asn Lys Asn Ser Ile Asp Ala Thr Asp Ile
                2245                2250                2255
Glu Asn Gly Val Asp Ser Thr Val Leu Glu Met Arg Val Ser Ala Asp
                2260                2265                2270
Ser Lys Ser Gly Phe Asn Gly Asp Gly Leu Glu Asn Ala Cys Arg Gly
            2275                2280                2285
Ala Gly Ile Phe Glu Gly Ile Arg Lys Asp Glu Trp Lys Cys Arg Asn
    2290                2295                2300
Val Cys Gly Tyr Val Val Cys Lys Pro Glu Asn Val Asn Gly Glu Ala
2305                2310                2315                2320
Lys Gly Lys His Ile Ile Gln Ile Arg Ala Leu Val Lys Arg Trp Val
                2325                2330                2335
Glu Tyr Phe Phe Glu Asp Tyr Asn Lys Ile Lys His Lys Ile Ser His
                2340                2345                2350
Arg Ile Lys Asn Gly Glu Ile Ser Pro Cys Ile Lys Asn Cys Val Glu
            2355                2360                2365
Lys Trp Val Asp Gln Lys Arg Lys Glu Trp Lys Glu Ile Thr Glu Arg
    2370                2375                2380
Phe Lys Asp Gln Tyr Lys Asn Asp Asn Ser Asp Asp Asp Asn Val Arg
2385                2390                2395                2400
Ser Phe Leu Glu Thr Leu Ile Pro Gln Ile Thr Asp Ala Asn Ala Lys
            2405                2410                2415
Asn Lys Val Ile Lys Leu Ser Lys Phe Gly Asn Ser Cys Gly Cys Ser
            2420                2425                2430
Ala Ser Ala Asn Glu Gln Asn Lys Asn Gly Glu Tyr Lys Asp Ala Ile
            2435                2440                2445
Asp Cys Met Leu Lys Lys Leu Lys Asp Lys Ile Gly Glu Cys Glu Lys
    2450                2455                2460
Lys His His Gln Thr Ser Asp Thr Glu Cys Ser Asp Thr Pro Gln Pro
2465                2470                2475                2480
Gln Thr Leu Glu Asp Glu Thr Leu Asp Asp Ile Glu Thr Glu Glu
            2485                2490                2495
Ala Lys Lys Asn Met Met Pro Lys Ile Cys Glu Asn Val Leu Lys Thr
                2500                2505                2510
Ala Gln Gln Glu Asp Glu Gly Gly Cys Val Pro Ala Glu Asn Ser Glu
            2515                2520                2525
Glu Pro Ala Ala Thr Asp Ser Gly Lys Glu Thr Pro Glu Gln Thr Pro
            2530                2535                2540
```

-continued

```
Val Leu Lys Pro Glu Glu Ala Val Pro Glu Pro Pro Pro Pro
2545                2550                2555                2560

Pro Gln Glu Lys Ala Pro Ala Pro Ile Pro Gln Pro Gln Pro Pro Thr
            2565                2570                2575

Pro Pro Thr Gln Leu Leu Asp Asn Pro His Val Leu Thr Ala Leu Val
            2580                2585                2590

Thr Ser Thr Leu Ala Trp Ser Val Gly Ile Gly Phe Ala Thr Phe Thr
            2595                2600                2605

Tyr Phe Tyr Leu Lys Val Asn Gly Ser Ile Tyr Met Gly Met Trp Met
            2610                2615                2620

Tyr Val Asp Val Cys Glu Cys Met Trp Met Tyr Val Asp Val Cys Gly
2625                2630                2635                2640

Cys Val Leu Trp Ile Cys Ile Cys Asp Tyr Val Trp Ile Tyr Ile Tyr
            2645                2650                2655

Ile Tyr Ile Cys Leu Cys Ile Cys Val Phe Gly Tyr Ile Tyr Val Tyr
            2660                2665                2670

Val Tyr Asp Phe Leu Tyr Met Tyr Leu Trp Val Lys Asp Ile Tyr Ile
            2675                2680                2685

Trp Met Tyr Leu Tyr Val Phe Tyr Ile Tyr Ile Leu Tyr Ile Cys Ile
            2690                2695                2700

Tyr Ile Lys Lys Glu Ile
2705                2710
```

(2) INFORMATION FOR SEQ ID NO: 13:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 13:

```
Cys Xaa Xaa Xaa Xaa Xaa Xaa Xaa Xaa Xaa Xaa Xaa Cys Xaa Xaa
1                   5                   10                  15

Xaa Xaa Xaa Val Cys Ile Pro Asp Arg Arg Tyr Gln Leu Cys Met Lys
            20                  25                  30

Glu Leu Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Asp Phe Cys Lys Asp Ile Arg Trp Ser Leu Gly Asp Phe Gly Asp
            85                  90                  95

Ile Ile Met Gly Thr Asp Met Glu Gly Ile Gly Tyr Ser Lys Xaa Xaa
            100                 105                 110

Xaa Xaa Xaa Xaa Xaa Xaa Xaa Xaa Thr Asp Glu Lys Ala Gln Gln
            115                 120                 125
```

```
Arg Arg Lys Gln Trp Trp Asn Glu Ser Lys Ala Gln Ile Trp Thr Ala
    130                 135                 140

Met Met Tyr Ser Val Xaa Xaa Xaa Xaa Xaa Xaa Xaa Xaa Xaa Xaa Xaa
145                 150                 155                 160

Cys Xaa Xaa Xaa Xaa Xaa Xaa Xaa Glu Pro Gln Ile Tyr Arg Trp
                165                 170                 175

Ile Arg Glu Trp Gly Arg Asp Tyr Val Ser Glu Leu Pro Thr Glu Val
            180                 185                 190

Gln Lys Leu Lys Glu Lys Cys Xaa Xaa Xaa Xaa Xaa Xaa Xaa Xaa
            195                 200                 205

Xaa Xaa Cys Xaa Val Pro Pro Cys Gln Asn Ala Cys Lys Ser Tyr Asp
    210                 215                 220

Gln Trp Ile Thr Arg Lys Lys Asn Xaa Xaa Xaa Xaa Xaa Xaa Xaa Xaa
225             230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
    275                 280                 285

Cys Xaa Cys
    290

(2) INFORMATION FOR SEQ ID NO: 14:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 14:

Cys Xaa Xaa Xaa Xaa Xaa Xaa Xaa Xaa Xaa Cys Xaa Xaa Xaa Xaa
1               5                   10                  15

Xaa Xaa Xaa Xaa Xaa Val Cys Ile Pro Asp Arg Arg Ile Gln Leu Cys
            20                  25                  30

Ile Val Asn Leu Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Lys Phe Cys Asn Asp Leu Lys Asn
65                  70                  75                  80

Ser Phe Leu Asp Tyr Gly His Leu Ala Met Gly Asn Asp Met Asp Phe
                85                  90                  95

Gly Gly Tyr Ser Thr Xaa Xaa Xaa Xaa Xaa Xaa Xaa Xaa Xaa Xaa
                100                 105                 110

Xaa Xaa Xaa Xaa Xaa Xaa Ser Glu His Lys Ile Lys Asn Phe Arg Lys
            115                 120                 125

Glu Trp Trp Asn Glu Phe Arg Glu Lys Leu Trp Glu Ala Met Leu Ser
```

```
            130                 135                 140
Glu His Xaa Xaa Xaa Xaa Xaa Cys Xaa Xaa Xaa Xaa Xaa Glu
145                 150                 155                 160

Leu Gln Ile Thr Gln Trp Ile Lys Glu Trp His Gly Glu Phe Leu Leu
                165                 170                 175

Glu Arg Asp Asn Arg Ser Lys Leu Pro Lys Ser Lys Cys Xaa Xaa Xaa
                180                 185                 190

Xaa Xaa Xaa Xaa Xaa Cys Xaa Glu Lys Glu Cys Ile Asp Pro Cys Met
            195                 200                 205

Lys Tyr Arg Asp Trp Ile Ile Arg Ser Lys Phe Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Cys Xaa Xaa Xaa Xaa Xaa Cys Xaa Cys
            260                 265                 270

(2) INFORMATION FOR SEQ ID NO: 15:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 15:

Cys Xaa Xaa Xaa Xaa Xaa Xaa Xaa Xaa Xaa Xaa Xaa Xaa Xaa Cys Xaa
1                   5                   10                  15

Xaa Xaa Xaa Xaa Xaa Xaa Xaa Xaa Xaa Val Cys Val Pro Pro Arg Arg
                20                  25                  30

Gln Glu Leu Cys Leu Gly Asn Ile Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Glu Val Cys Lys
65                  70                  75                  80

Ile Ile Asn Lys Thr Phe Ala Asp Ile Arg Asp Ile Ile Gly Gly Thr
                85                  90                  95

Asp Tyr Trp Asn Asp Leu Ser Asn Arg Xaa Xaa Xaa Xaa Xaa Xaa Xaa
                100                 105                 110

Xaa Xaa Xaa Xaa Xaa Xaa Xaa Xaa Asn Lys Lys Asn Asp Lys Leu Phe
                115                 120                 125

Arg Asp Glu Trp Trp Lys Val Ile Lys Lys Asp Val Trp Asn Val Ile
                130                 135                 140

Ser Trp Phe Xaa Xaa Xaa Xaa Xaa Cys Xaa Xaa Xaa Xaa Xaa Xaa Xaa
145                 150                 155                 160

Ile Pro Gln Phe Phe Arg Trp Phe Ser Glu Trp Gly Asp Asp Tyr Cys
                165                 170                 175
```

```
Gln Asp Lys Thr Lys Met Ile Glu Thr Leu Lys Val Glu Cys Xaa Xaa
            180                 185                 190

Xaa Xaa Cys Xaa Asp Asp Asn Cys Lys Ser Lys Cys Asn Ser Tyr Lys
        195                 200                 205

Glu Trp Ile Ser Lys Lys Lys Xaa Xaa Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Cys Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Cys Xaa Xaa Cys
            275

(2) INFORMATION FOR SEQ ID NO: 16:

(i) SEQUENCE CHARACTERISTICS:
        (A) LENGTH: 282 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 16:

Cys Xaa Xaa Xaa Xaa Xaa Xaa Xaa Xaa Xaa Xaa Xaa Cys Xaa Xaa
1               5                   10                  15

Xaa Xaa Xaa Xaa Xaa Xaa Xaa Xaa Xaa Val Cys Gly Pro Pro Arg Arg
            20                  25                  30

Gln Gln Leu Cys Leu Gly Tyr Ile Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Lys Ile Cys Asn
65                  70                  75                  80

Ala Ile Leu Gly Ser Tyr Ala Asp Ile Gly Asp Ile Val Arg Gly Leu
                85                  90                  95

Asp Val Trp Arg Asp Ile Asn Thr Asn Xaa Xaa Xaa Xaa Xaa Xaa
            100                 105                 110

Xaa Xaa Xaa Xaa Xaa Xaa Xaa Xaa Xaa Lys Lys Gln Asn Asp Asn
            115                 120                 125

Asn Glu Arg Asn Lys Trp Trp Glu Lys Gln Arg Asn Leu Ile Trp Ser
    130                 135                 140

Ser Met Val Lys His Ile Xaa Xaa Xaa Xaa Xaa Cys Xaa Xaa Xaa Xaa
145                 150                 155                 160

Xaa Xaa Xaa Xaa Ile Pro Gln Phe Leu Arg Trp Leu Lys Glu Trp Gly
            165                 170                 175

Asp Glu Phe Cys Glu Glu Met Gly Thr Glu Val Lys Gln Leu Glu Lys
            180                 185                 190
```

```
Ile Cys Xaa Xaa Xaa Xaa Cys Xaa Glu Lys Lys Cys Lys Asn Ala Cys
        195                 200                 205

Ser Ser Tyr Glu Lys Trp Ile Lys Glu Arg Lys Asn Xaa Xaa Xaa Xaa
210             215                 220

Xaa Xaa Xaa Xaa Xaa Xaa Xaa Xaa Xaa Xaa Xaa Xaa Xaa Xaa Xaa Xaa
225             230                 235                 240

Xaa Xaa Xaa Xaa Xaa Xaa Xaa Xaa Xaa Xaa Xaa Xaa Xaa Xaa Xaa Xaa
            245                 250                 255

Xaa Xaa Cys Xaa Xaa Xaa Xaa Xaa Xaa Xaa Xaa Xaa Xaa Xaa Xaa Xaa
        260                 265                 270

Xaa Xaa Xaa Xaa Xaa Xaa Cys Xaa Xaa Cys
275                 280
```

(2) INFORMATION FOR SEQ ID NO: 17:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 17:

```
Cys Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Xaa Xaa Ala Cys Ile Pro Pro Arg Arg Gln Lys
            20                  25                  30

Leu Cys Leu His Tyr Leu Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Asp Phe Lys Arg Gln Met Phe
                85                  90                  95

Tyr Thr Phe Ala Asp Tyr Arg Asp Ile Cys Leu Gly Thr Asp Ile Ser
            100                 105                 110

Ser Lys Lys Asp Thr Ser Xaa Xaa Xaa Xaa Xaa Xaa Xaa Xaa Xaa Xaa
        115                 120                 125

Xaa Xaa Xaa Xaa Xaa Lys Ile Ser Asn Ser Ile Arg Tyr Arg Lys Ser
130                 135                 140

Trp Trp Glu Thr Asn Gly Pro Val Ile Trp Glu Gly Met Leu Cys Ala
145                 150                 155                 160

Leu Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Arg Pro Gln Phe Leu
                195                 200                 205

Arg Trp Leu Thr Glu Trp Gly Glu Asn Phe Cys Lys Glu Gln Lys Lys
```

-continued

```
        210                 215                 220
Glu Tyr Lys Val Leu Leu Ala Lys Cys Xaa Xaa Xaa Xaa Xaa Xaa
225                 230                 235                 240

Xaa Xaa Xaa Xaa Cys Xaa Xaa Xaa Cys Val Ala Cys Lys Asp Gln Cys
            245                 250                 255

Lys Gln Tyr His Ser Trp Ile Gly Ile Trp Ile Asp Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Cys Xaa Xaa Xaa Xaa Xaa Xaa Xaa Xaa Cys
305                 310                 315                 320

Xaa Xaa Xaa Cys
```

(2) INFORMATION FOR SEQ ID NO: 18:

(i) SEQUENCE CHARACTERISTICS:
        (A) LENGTH: 362 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 18:

```
Ala Cys Ala Pro Tyr Arg Arg Leu His Leu Cys Asp Tyr Asn Leu Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Gln Leu Cys Thr Val Leu
        50                  55                  60

Ala Arg Ser Phe Ala Asp Ile Gly Asp Ile Val Arg Gly Lys Asp Leu
65                  70                  75                  80

Tyr Leu Gly Tyr Asp Asn Lys Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Lys Gly Gly Asp
            115                 120                 125

Phe Phe Gln Leu Arg Glu Asp Trp Trp Thr Ser Asn Arg Glu Thr Val
130                 135                 140

Trp Lys Ala Leu Ile Cys His Ala Xaa Xaa Xaa Xaa Xaa Xaa Xaa
145                 150                 155                 160

Xaa Xaa Xaa Cys Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Val Pro Gln Tyr Leu
            180                 185                 190
```

```
Arg Trp Phe Glu Glu Trp Ala Glu Asp Phe Cys Arg Lys Lys Lys
        195                 200                 205

Lys Leu Glu Asn Leu Gln Lys Gln Cys Xaa Xaa Xaa Xaa Xaa Cys
        210                 215                 220

Xaa Xaa Xaa Xaa Xaa Xaa Xaa Xaa Xaa Xaa Xaa Xaa Xaa Xaa Cys
225                 230                 235                 240

Thr Asn Cys Ser Val Trp Cys Arg Met Tyr Glu Thr Trp Ile Asp Asn
                245                 250                 255

Gln Lys Lys Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Cys Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Cys Xaa Xaa Cys
            355                 360
```

(2) INFORMATION FOR SEQ ID NO: 19:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 19:

```
Cys Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Xaa Xaa Xaa Xaa Xaa Xaa Xaa Xaa
            20                  25                  30

Ala Cys Ala Pro Tyr Arg Arg Leu His Val Cys Asp Gln Asn Leu Xaa
            35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Gln Ile Cys Thr
            85                  90                  95

Met Leu Ala Arg Ser Phe Ala Asp Ile Gly Asp Ile Val Arg Gly Arg
            100                 105                 110

Asp Leu Tyr Leu Gly Asn Pro Gln Glu Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
```

-continued

```
            130                 135                 140
Xaa Xaa Xaa Xaa Xaa Xaa Asn Asp Pro Glu Phe Phe Lys Leu Arg
145                 150                 155                 160

Glu Asp Trp Trp Thr Ala Asn Arg Glu Thr Val Trp Lys Ala Ile Thr
                165                 170                 175

Cys Asn Ala Xaa Xaa Xaa Xaa Xaa Xaa Xaa Cys Xaa Xaa Xaa
                180                 185                 190

Xaa Xaa Xaa Xaa Xaa Xaa Xaa Xaa Xaa Xaa Xaa Xaa Xaa Xaa
            195                 200                 205

Xaa Xaa Xaa Xaa Val Pro Gln Tyr Leu Arg Trp Phe Glu Trp Ala
    210                 215                 220

Glu Asp Phe Cys Arg Lys Lys Asn Lys Lys Ile Lys Asp Val Lys Arg
225                 230                 235                 240

Asn Cys Xaa Xaa Xaa Xaa Xaa Xaa Xaa Xaa Xaa Xaa Cys Xaa
                245                 250                 255

Xaa Xaa Xaa Xaa Xaa Xaa Xaa Xaa Xaa Xaa Xaa Xaa Xaa Xaa
            260                 265                 270

Xaa Xaa Xaa Xaa Xaa Cys Ile Ser Cys Leu Tyr Ala Cys Asn Pro Tyr
    275                 280                 285

Val Asp Trp Ile Asn Asn Gln Lys Glu Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Cys Xaa
            355                 360                 365

Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
                405                 410
```

(2) INFORMATION FOR SEQ ID NO: 20:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 20:

```
Cys Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Xaa Xaa Xaa Xaa Xaa Xaa
            20                  25                  30
```

Xaa Xaa Xaa Xaa Xaa Xaa Xaa Xaa Xaa Xaa Xaa Xaa Xaa Xaa Xaa
            35                  40                  45

Xaa Xaa Val Phe Leu Pro Pro Arg Arg Glu His Met Cys Thr Ser Asn
        50                  55                  60

Leu Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Ala Met Cys Arg Ala Val Arg Tyr
            115                 120                 125

Ser Phe Ala Asp Leu Gly Asp Ile Ile Arg Gly Arg Asp Met Trp Asp
            130                 135                 140

Glu Asp Lys Ser Ser Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Lys Lys Pro Ala Tyr Lys Lys Leu Arg Ala Asp
            180                 185                 190

Trp Trp Glu Ala Asn Arg His Gln Val Trp Arg Ala Met Lys Cys Ala
            195                 200                 205

Thr Xaa Xaa Xaa Xaa Cys Xaa Xaa Xaa Xaa Xaa Xaa Xaa Ile Pro
            210                 215                 220

Gln Arg Leu Arg Trp Met Thr Glu Trp Ala Glu Trp Tyr Cys Lys Ala
225                 230                 235                 240

Gln Ser Gln Glu Tyr Asp Lys Leu Lys Lys Ile Cys Xaa Xaa Xaa Xaa
            245                 250                 255

Xaa Xaa Xaa Xaa Xaa Xaa Xaa Cys Xaa Xaa Xaa Xaa Xaa Xaa Cys Gly
            260                 265                 270

Lys Cys Lys Ala Ala Cys Asp Lys Tyr Lys Glu Glu Ile Glu Lys Trp
            275                 280                 285

Asn Glu Gln Trp Arg Lys Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Cys
            355                 360                 365

Xaa Xaa Xaa Xaa Xaa Xaa Cys Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
            405                 410

(2) INFORMATION FOR SEQ ID NO: 21:

(i) SEQUENCE CHARACTERISTICS:
        (A) LENGTH: 311 amino acids
        (B) TYPE: amino acid (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 21:

Cys Xaa Xaa Xaa Xaa Xaa Xaa Xaa Xaa Cys Xaa Xaa Xaa Xaa
 1               5                  10                  15

Xaa Xaa Xaa Xaa Xaa Xaa Ala Cys Met Pro Pro Arg Arg Gln Lys Leu
            20                  25                  30

Cys Leu Tyr Tyr Ile Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Gln Phe Leu Arg Ser Met Met
                 85                  90                  95

Tyr Thr Phe Gly Asp Tyr Arg Asp Ile Cys Leu Asn Thr Asp Ile Ser
                100                 105                 110

Lys Lys Gln Asn Asp Val Xaa Xaa Xaa Xaa Xaa Xaa Xaa Xaa Xaa
            115                 120                 125

Xaa Xaa Xaa Xaa Xaa Ser Lys Ser Pro Ser Gly Leu Ser Arg Gln Glu
        130                 135                 140

Trp Trp Lys Thr Asn Gly Pro Glu Ile Trp Lys Gly Met Leu Cys Ala
145                 150                 155                 160

Leu Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Lys Pro Gln Phe Leu Arg Trp Met Ile Glu
            195                 200                 205

Trp Gly Glu Glu Phe Cys Ala Glu Arg Gln Lys Lys Glu Asn Ile Ile
210                 215                 220

Lys Asp Ala Cys Xaa Xaa Xaa Xaa Xaa Xaa Xaa Cys Xaa Xaa Xaa
225                 230                 235                 240

Lys His Arg Cys Asn Gln Ala Cys Arg Ala Tyr Gln Glu Tyr Val Glu
                245                 250                 255

Asn Lys Lys Lys Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Cys
    290                 295                 300

Xaa Xaa Xaa Xaa Cys Xaa Cys
305                 310

(2) INFORMATION FOR SEQ ID NO: 22:

(i) SEQUENCE CHARACTERISTICS:

```
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 22:

Pro Arg Arg Gln Xaa Leu Cys
 1               5

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

CCRAGRAGRC AARAAYTATG                                              20

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

CCSMGSMGSC AGCAGYTSTG                                              20

(2) INFORMATION FOR SEQ ID NO: 25:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO
```

(iv) ANTI-SENSE: NO (v) FRAGMENT TYPE: N-terminal (vi) ORIGINAL SOURCE:

(xi) SEQUENCE DESCRIPTION: SEQ ID NO: 25:

Phe Ala Asp Xaa Xaa Asp Ile
 1               5

(2) INFORMATION FOR SEQ ID NO: 26:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

TTTGCWGATW WWSGWGATAT                                                    20

(2) INFORMATION FOR SEQ ID NO: 27:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

TTCGCSGATW WCSGSGACAT                                                    20

(2) INFORMATION FOR SEQ ID NO: 28:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 28:

Pro Gln Phe Xaa Arg Trp (2) INFORMATION FOR SEQ ID NO: 29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

CCAWCKKARR AATTGWGG                                      18

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

CCASCKGWAG AWCTGSGG                                      18

(2) INFORMATION FOR SEQ ID NO: 31:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 31:

Glu Trp Gly Xaa Xaa Xaa Cys
 1           5

(2) INFORMATION FOR SEQ ID NO: 32:

(i) SEQUENCE CHARACTERISTICS:
        (A) LENGTH: 20 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 32:

CAAWAWTCWT CWCCCCATTC                                              20

(2) INFORMATION FOR SEQ ID NO: 33:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 33:

CAGWASTCST CSCCCCACTC                                              20

(2) INFORMATION FOR SEQ ID NO: 34:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 34:

ATCGATCAGC TGGGAAGAAA TACTTCATCT                                   30

(2) INFORMATION FOR SEQ ID NO: 35:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 35:

ATCGATGGGC CCCGAAGTTT GTTCATTATT                    30

(2) INFORMATION FOR SEQ ID NO: 36:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 36:

TCTCGTCAGC TGACGATCTC TAGTGCTATT                    30

(2) INFORMATION FOR SEQ ID NO: 37:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 37:

ACGAGTGGGC CCTGTCACAA CTTCCTGAGT                    30

BINDING DOMAINS FROM *PLASMODIUM VIVAX* AND *PLASMODIUM FALCIPARUM* ERYTHROCYTE BINDING PROTEINS

This application is a continuation of prior application Ser. No. 09/210,288, filed Dec. 11, 1998, now U.S. Pat. No. 6,392,026, which is a divisional of U.S. patent application Ser. No. 08/568,459, filed Dec. 7, 1995, now U.S. Pat. No. 5,849,306, which is a continuation of U.S. patent application Ser. No. 08/119,677, filed Sep. 10, 1993, abandoned.

BACKGROUND OF THE INVENTION

Malaria infects 200–400 million people each year causing 1–2 million deaths, thus remaining one of the most important infectious diseases in the world. Approximately 25 percent of all deaths of children in rural Africa between the ages of one and four years are caused by malaria. Due to the importance of the disease as a worldwide health problem, considerable effort is being expended to identify and develop malaria vaccines.

Malaria in humans is caused by four species of the parasite *Plasmodium*: *P. falciparum*, *P. vivax*, *P. knowlesi* and *P. malariae*. The major cause of malaria in humans if *P. falciparum* which infects 200 million to 400 million people every year, killing 1 to 4 million.

*P. vivax* (one of the four species infective to humans) cannot be cultured in vitro, as has been possible with *P. knowlesi* (a malarial strain found in old world monkeys which also invade human erythrocytes) and *P. falciparum*. Although *P. vivax* bears substantial phylogenetic similarity to *P. knowlesi*, the two species are different in many important respects. For example, *P. vivax* is not infective of many simian species and infection is poorly established in others, whereas *P. knowlesi* is poorly infective of humans while readily infecting many simian species.

The basis of various potential vaccines to combat malaria is appreciated through an understanding of the life cycle of the parasite. Infection in humans begins when young malarial parasites or "sporozoites" are injected into the bloodstream of a human by the mosquito. Following injection, the parasite localizes to liver cells. After approximately one week the parasites or "merozoites" are released into the bloodstream. The entry of the parasites into the bloodstream begins the "erythrocytic" phase. Each parasite enters the red blood cell in order to grow and develop. When the merozoite matures in the red blood cell, it is known as a trophozoite. The trophozoite undergoes several rounds of nuclear division (schizogony) until it ruptures the erythrocyte, releasing from 6 to 24 merozoites. After several asexual schizogonic cycles, some parasites, instead of becoming schizonts through asexual reproduction, develop into morphologically distinct forms known as "gametocytes" which are long-lived and undergo sexual development.

Sexual development of the malaria parasites involve the female or "macrogametocyte" and the male parasite or "microgametocyte." These gametocytes do not undergo any further development in humans. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs upon fusion of the microgamete and the macrogamete. The fertilized parasite is known as a zygote which develops into an "ookinete." The ookinete embeds in the midgut of the mosquito, transforming into an oocyst within which many small sporozoites form. Before embedding in the midgut, the ookinete must first penetrate the peritrophic membrane which apparently acts as a barrier for invasion of ingested parasites. When the oocyst ruptures the sporozoites migrate to the salivary gland of the mosquito via the hemolymph. Once in the saliva of the mosquito, the parasite can be injected into a host.

The erythrocytic stage of the *Plasmodium* life cycle is of special relevance to vaccine development because the clinical and pathologic features of malaria in the host are attributable to this stage. In *P. vivax*, and *P. knowlesi*, Duffy blood group determinants present on Duffy positive erythrocytes are essential for invasion of human erythrocytes (Miller et al., Science 189: 561–563, (1975); Miller et al., N. Engl. J. Med. 295: 302–304, (1976)). In *P. falciparum*, invasion of merozoites into erythrocytes appears to be dependent on binding to sialic acids on glycophorins on the erythrocyte (Miller, et al., J. Exp. Med. 146: 277–281, (1971); Pasvol, et al., Lancet. ii: 947–950 (1982); Pasvol, et al., Nature, 279: 64–66 (1982); Perkins, J. Exp. Med. 160: 788–798 (1984)). Studies with the monkey parasite *P. knowlesi* allow a clearer understanding of the multiple events that occur during invasion. It is likely that even though *P. vivax* and *P. falciparum* bind to the Duffy antigen and sialic acids respectively, they share common strategies of invasion with each other and with *P. knowlesi*.

In *P. knowlesi*, during invasion a merozoite first attaches to an erythrocyte on any surface of the merozoite, then reorients so that its apical end is in contact with the erythrocyte (Dvorak et al., Science 187: 748–750, (1975)). Both attachment and reorientation of merozoites occur equally well on Duffy positive and Duffy negative cells. A junction then forms between the apical end of the merozoite and the Duffy positive erythrocyte followed by vacuole formation and entry of the merozoite into the vacuole. Aikawa et al., J. Cell Biol. 77: 72–82 (1978). Junction formation and merozoite entry into the erythrocyte do not occur on Duffy negative cells (Miller et al., J. Exp. Med. 149: 172–184 (1979)), suggesting that a receptor specific for the Duffy determinant is involved in apical junction formation but not initial attachment.

The apical end of the merozoite is defined by the presence of three organelles: rhopteries, dense, granules and micronemes. The rhopteries and dense granules release their contents at vacuole formation (Ladda et al., 1969; Aikawa et al., J. Cell Biol., 77: 72–82 (1978); Torn et al., Infection and Immunity 57: 3230–3233 (1989); Bannister and Dluzewski, Blood Cells 16: 257–292 (1990)). To date the function of the microneme is unknown. Nevertheless, the location of the micronemes suggest that they are involved in the invasion process. Duffy Antigen Binding Protein (DABP) and Sialic Acid Binding Protein (SABP) have been localized to the micronemes of *P. knowlesi* and *P. falciparum* respectively (Adams et al., Cell 63: 141–153 (1990); Sim et al., Mol. Biochem. Parasitol. 51: 157–160 (1992)).

DABP and SABP are soluble proteins that appear in the culture supernatant after infected erythrocytes release merozoites. Immunochemical data indicate that DABP and SABP which are the respective ligands for the *P. vivax* and *P. falciparum* Duffy and sialic acid receptors on erythrocytes, possess specificities of binding which are identical either in soluble or membrane bound form.

DABP is a 135 kDa protein which binds specifically to Duffy blood group determinants (Wertheimer et al., Exp. Parasitol. 69: 340–350 (1989); Barnwell, et al., J. Exp. Med.

169: 1795–1802 (1989)). Thus, binding of DABP is specific to human Duffy positive erythrocytes. There are four major Duffy phenotypes for human erythrocytes: Fy(a), Fy(b), Fy(ab) and Fy(negative), as defined by the anti-$Fy^a$ and anti-$Fy^b$ sera (Hadley et al., In Red Cell Antigens and Antibodies, G. Garratty, ed. (Arlington, Va.: American Association of Blood Banks) pp. 17–33 (1986)). DABP binds equally to both Fy(a) and Fy(b) erythrocytes which are equally susceptible to invasion by *P. vivax*; but not to Fy(negative) erythrocytes.

In the case of SABP, a 175 kDa protein, binding is specific to the glycophorin sialic acid residues on erythrocytes (Camus and Hadley, Science 230:553–556 (1985); Orlandi, et al., J. Cell Biol. 116:901–909 (1992)). Thus, neuraminidase treatment (which cleaves off sialic acid residues) render erythrocytes immune to *P. falciparum* invasion.

The specificities of binding and correlation to invasion by the parasite thus indicate that DABP and SABP are the proteins of *P. vivax* and *P. falciparum* which interact with sialic acids and the Duffy antigen on the erythrocyte. The genes encoding both proteins have been cloned and the DNA and predicted protein sequences have been determined (B. Kim Lee Sim, et al., J. Cell Biol. 111: 1877–1884 (1990); Fang, X., et al., Mol. Biochem Parasitol. 44: 125–132 (1991)).

Despite considerable research efforts worldwide, because of the complexity of the *Plasmodium* parasite and its interaction with its host, it has not been possible to discover a satisfactory solution for prevention or abatement of the blood stage of malaria. Because malaria is a such a large worldwide health problem, there is a need for methods that abate the impact of this disease. The present invention provides effective preventive and therapeutic measures against *Plasmodium* invasion.

SUMMARY OF THE INVENTION

The present invention provides compositions comprising an isolated DABP binding domain polypeptides and/or isolated SABP binding domain polypeptides. The DABP binding domain polypeptides preferably comprise between about 200 and about 300 amino acid residues while the SABP binding domain polypeptides preferably comprises between about 200 and about 600 amino acid residues. A preferred DABP binding domain polypeptide has residues 1 to about 325 of the amino acid sequence found in SEQ ID No. 2. A preferred SABP binding domain polypeptide has residues 1 to about 616 of the amino acid sequence of SEQ ID No. 4.

The present invention also includes pharmaceutical compositions comprising a pharmaceutically acceptable carrier and an isolated DABP binding domain polypeptide in an amount sufficient to induce a protective immune response to *Plasmodium vivax* merozoites in an organism. In addition, isolated SABP binding domain polypeptide in an amount sufficient to induce protective immune response to *Plasmodium falciparum* may be added to the pharmaceutical composition.

Also provided are pharmaceutical compositions comprising a pharmaceutically acceptable carrier and an isolated SABP binding domain polypeptide in an amount sufficient to induce a protective immune response to *Plasmodium falciparum* merozoites in an organism. In addition, isolated DABP binding domain polypeptide in an amount sufficient to induce a protective immune response to *Plasmodium vivax* may be added to the pharmaceutical composition.

Isolated polynucleotides which encode a DABP binding domain polypeptides or SABP binding domain polypeptides are also disclosed. In addition, the present invention includes a recombinant cell comprising the polynucleotide encoding the DABP binding domain polypeptide.

The current invention further includes methods of inducing a protective immune response to *Plasmodium* merozoites in a patient. The methods comprise administering to the patient an immunologically effective amount of a pharmaceutical composition comprising a pharmaceutically acceptable carrier and an isolated DABP binding domain polypeptide, an SABP binding domain polypeptide or a combination thereof.

The present disclosure also provides DNA sequences from additional *P. falciparum* genes in the erythrocyte binding ligand (EBL) family that have regions conserved with the *P. falciparum* 175 kD and *P. vivax* 135 kD binding proteins.

DEFINITIONS

As used herein a "DABP binding domain polypeptide" or a "SABP binding domain polypeptide" are polypeptides substantially identical (as defined below) to a sequence from the cysteine-rich, amino-terminal region of the Duffy antigen binding protein (DABP) or sialic acid binding protein (SABP), respectively. Such polypeptides are capable of binding either the Duffy antigen or sialic acid residues on glycophorin. In particular, DABP binding domain polypeptides consist of amino acid residues substantially similar to a sequence of SABP within a binding domain from the N-terminal amino acid (residue 1) to about residue 325. SABP binding domain polypeptides consist of residues substantially similar to a sequence of DABP within a binding domain from the N-terminal amino acid (residue 1) to about residue 616.

The binding domain polypeptides encoded by the genes of the EBL family consist of those residues substantially identical to the sequence of the binding domains of DABP and SABP as defined above. The EBL family comprises sequences with substantial similarity to the conserved regions of the DABP and SABP. These include those sequences reported here as EBL-e1 (SEQ ID NOs 5 and 6), E31a (SEQ ID NOs 7 and 8), EBL-e2 (SEQ ID NOs 9 and 10) and Proj3 (SEQ ID NOs 11 and 12).

The polypeptides of the invention can consist of the full length binding domain or a fragment thereof. Typically DABP binding domain polypeptides will consist of from about 50 to about 325 residues, preferably between about 75 and 300, more preferably between about 100 and about 250 residues. SABP binding domain polypeptides will consist of from about 50 to about 616 residues, preferably between about 75 and 300, more preferably between about 100 and about 250 residues.

Particularly preferred polypeptides of the invention are those within the binding domain that are conserved between SABP and the EBL family. Residues within these conserved domains are shown in FIG. 1, below.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The term "substantial identity" means that a polypeptide comprises a sequence that has at least 80% sequence identity, preferably 90%, more preferably 95% or more, compared to a reference sequence over a comparison window of about 20 residues to about 600 residues—typically about 50 to about 500 residues usually about 250 to 300 residues. The values of percent identity are determined using the programs above. Particularly preferred peptides of the present invention comprise a sequence in which at least 70% of the cysteine residues conserved in DABP and SABP are present. Additionally, the peptide will comprise a sequence in which at least 50% of the Tryptophan residues conserved in DABP and SABP are present. The term substantial similarity is also specifically defined here with respect to those amino acid residues found to be conserved between DABP, SABP and the sequences of the EBL family. These conserved amino acids consist prominently of tryptophan and cysteine residues conserved among all sequences reported here. In addition the conserved amino acid residues include phenylalanine residues which may be substituted with tyrosine. These amino acid residues may be determined to be conserved after the sequences have been aligned using methods outlined above by someone skilled in the art.

Another indication that polypeptide sequences are substantially identical is if one protein is immunologically reactive with antibodies raised against the other protein. Thus, the polypeptides of the invention include polypeptides immunologically reactive with antibodies raised against the SABP binding domain, the DABP binding domain or raised against the conserved regions of the EBL family.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

The phrases "isolated" or "biologically pure" refer to material which is substantially or essentially free from components which normally accompany it as found in its native state. Thus, the binding domain polypeptides of this invention do not contain materials normally associated with their in situ environment, e.g., other proteins from a merozoite membrane. However, even where a protein has been isolated to a homogenous or dominant band by PAGE, there can be trace contaminants in the range of 5–10% of native protein which co-purify with the desired protein. Isolated polypeptides of this invention do not contain such endogenous co-purified protein.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

DESCRIPTION OF THE PREFERRED EMBODIMENT

Figure 1:
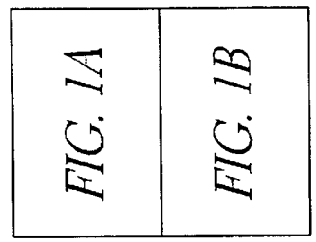
FIG. 1 represents an alignment of the predicted amino acid sequences of the DABP binding domain (Vivax), the two homologous SABP domains (SABP F1 and SABP F2) and the sequenced members of the EBL gene family (ebl-e1, E31a, EBL-e2 and the three homologous Proj3 domains.
Figure 2:
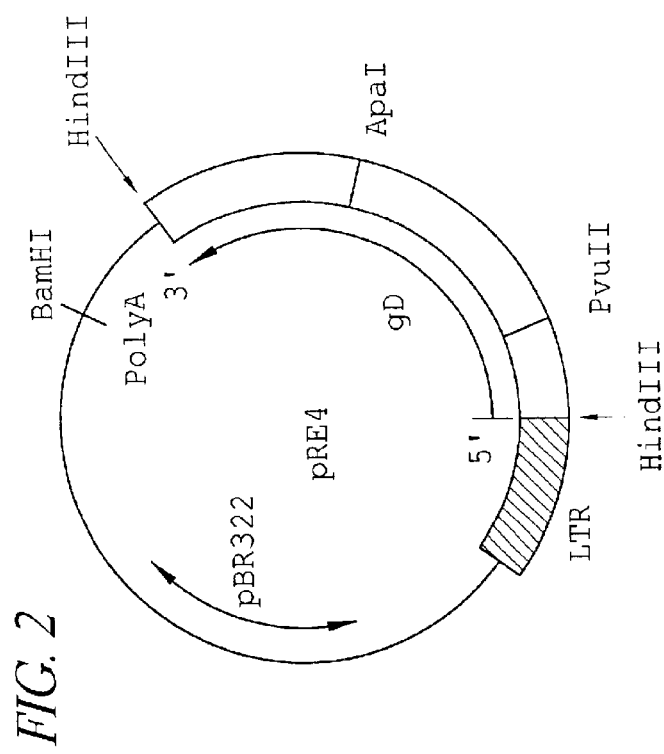
FIG. 2 represents a schematic of the pRE4 cloning vector.

The binding of merozoites and schizonts to erythrocytes is mediated by specific binding proteins on the surface of the merozoite or schizont and is necessary for erythrocyte invasion. In the case of *P. falciparum*, this binding involves specific interaction between sialic acid glycophorin residues on the erythrocyte and the sialic acid binding protein (SABP) on the surface of the merozoite or schizont. The ability of purified SABP to bind erythrocytes with chemically or enzymatically altered sialic acid residues paralleled the ability of *P. falciparum* to invade these erythrocytes. Furthermore, sialic acid deficient erythrocytes neither bind SABP nor support invasion by *P. falciparum*. The DNA encoding SABP from *P. falciparum* has also been cloned and sequenced.

In *P. vivax*, specific binding to the erythrocytes involves interaction between the Duffy blood group antigen on the erythrocyte and the Duffy antigen binding protein (DABP) on the merozoite. Duffy binding proteins were defined biologically as those soluble proteins that appear in the culture supernatant after the infected erythrocytes release merozoites which bind to human Duffy positive, but not to human Duffy negative erythrocytes. It has been shown that binding of the *P. vivax* DABP protein to Duffy positive erythrocytes is blocked by antisera to the Duffy blood group determinants. Purified Duffy blood group antigens also block the binding to erythrocytes. DABP has also been shown to bind Duffy blood group determinants on Western blots.

Duffy positive blood group determinants on human erythrocytes are essential for invasion of human erythrocytes by *Plasmodium vivax*. Both attachment and reorientation of *P. vivax* merozoites occur equally well on Duffy positive and negative erythrocytes. A junction then forms between the apical end of the merozoite and the Duffy-positive erythrocyte, followed by vacuole formation and entry of the merozoite into the vacuole. Junction formation and merozoite entry into the erythrocyte do not occur on Duffy negative cells, suggesting that the receptor specific for the Duffy determinant is involved in apical junction formation but not initial attachment. The DNA sequences encoding the DABP from *P. vivax* and *P. knowlesi* have been cloned and sequenced.

*P. vivax* red cell invasion has an absolute requirement for the. Duffy blood group antigen. Isolates of *P. falciparum*, however, vary in their dependency on sialic acid for invasion. Certain *P. falciparum* clones have been developed which invade sialic acid deficient erythrocytes at normal rates. This suggests that certain strains of *P. falciparum* can interact with other ligands on the erythrocyte and so may possess multiple erythrocyte binding proteins with differing specificities.

A basis for the present invention is the discovery of the binding domains in both DABP and SABP. Comparison of the predicted protein sequences of DABP and SABP reveals an amino-terminal, cysteine-rich region in both proteins with a high degree of similarity between the two proteins. The amino-terminal, cysteine-rich region of DABP contains about 325 amino acids, whereas the amino-terminal, cysteine-rich region of SABP contains about 616 amino acids. This is due to an apparent duplication of the amino-terminal, cysteine-rich region in the SABP protein. The cysteine residues are conserved between the two regions of SABP and DABP, as are the amino acids surrounding the cysteine residues and a number of aromatic amino acid residues in this region. The amino-terminal cysteine rich region and another cysteine-rich region near the carboxyl-terminus show the most similarity between the DABP and SABP proteins. The region of the amino acid sequence between these two cysteine-rich regions show only limited similarity between DABP and SABP.

Other *P. falciparum* open reading frames and genes with regions that have substantial identity to binding domains of SABP and DABP have been identified. Multiple copies of these sequences-exist in the parasite genome, indicating their important activity in host-parasite interactions. A family of these sequences (the EBL family) have been cloned from chromosome 7 subsegment libraries that were constructed during genetic studies of the chloroquine resistance locus (Wellems et. al., *PNAS* 88: 3382–3386 (1991)). Alignment of EBL sequences identified domains highly conserved with the *P. falciparum* 175 kD protein; these conserved domains have in turn been used to identify genes (ebl-e1, ebl-e2) one of which (ebl-e1) resides on chromosome 13. Genetic linkage studies have placed this gene within a region of chromosome 13 that affects invasion of malarial parasites in human red blood cells (Wellems et al., *Cell* 49:633–642 (1987)).

Southern hybridization experiments using probes from these open reading frames have indicated that additional copies of these conserved sequences are located elsewhere in the genome. The largest of the open reading frames on chromosome 7 is 8 kilobases and contains four tandem repeats homologous to the N-terminal, cysteine-rich unit of SABP and DABP.

FIG. 1 represents an alignment of the EBL family with the DABP binding domain and two homologous regions of SABP ($F_1$ and $F_2$). The EBL family is divided into two sub-families to achieve optimal alignment. Conserved cysteine residues are shown in bold face and conserved aromatic residues are underlined.

The polypeptides of the invention can be used to raise monoclonal antibodies specific for the binding domains of SABP, DABP or the conserved regions in the EBL gene family. The antibodies can be used for diagnosis of malarial infection or as therapeutic agents to inhibit binding of merozoites to erythrocytes. The production of monoclonal antibodies against a desired antigen is well known to those of skill in the art and is not reviewed in detail here.

The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and F(ab)$_2$, as well as in single chains. For a general review of immunoglobulin structure and function see, *Fundamental Immunology*, 2d Ed., W. E. Paul ed., Ravens Press, N.Y., (1989).

Antibodies which bind polypeptides of the invention may be produced by a variety of means. The production of non-human monoclonal antibodies, e.g., murine, lagomorpha, equine, etc., is well known and may be accomplished by, for example, immunizing the animal with a preparation containing the polypeptide. Antibody-producing cells obtained from the immunized animals are immortalized and screened, or screened first for the production of antibody which inhibits binding between and meroxoites and erythrocytes and then immortalized. For a discussion of general procedures of monoclonal antibody production see Harlow and Lane, *Antibodies, A Laboratory Manual* Cold Spring Harbor Publications, N.Y. (1988).

Thus, the present invention allows targeting of protective immune responses or monoclonal antibodies to sequences in the binding domains that are conserved between SABP, DABP and encoded regions of the EBL family. Identification of the binding regions of these proteins facilitates vaccine development because it allows for a focus of effort upon the functional elements of the large molecules. The particular sequences within the binding regions refine the target to critical regions that have been conserved during evolution, and are thus preferred for use as vaccines against the parasite.

The genes of the EBL family (which have not previously been sequenced) can be used as markers to detect the presence of the *P. falciparum* parasite in patients. This can be accomplished by means well known to practitioners in the art using tissue or blood from symptomatic patients in PCR reactions with oligonucleotides complementary to portions of the genes of the EBL family. Furthermore, sequencing the EBL family provides a means for skilled practitioners to generate defined probes to be used as genetic markers in a variety of applications.

Figure 3:
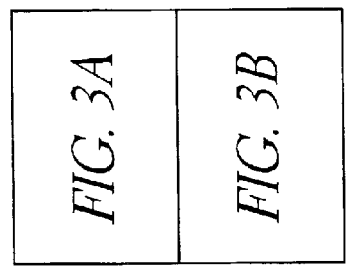
FIG. 3 shows primers useful for isolating sequences encoding the conserved motifs of the invention.

Additionally, the present invention defines a conserved motif present in, but not restricted to other members of the subphylum Apicomplexa which participates in host parasite interaction. This motif can be identified in *Plasmodium* species and other parasitic protozoa by the polymerase chain reaction using the synthetic oligonucleotide primers shown in FIG. 3. PCR methods are described in detail below. These primers are designed from regions in the conserved motif showing the highest degree of conservation among DABP, SABP and the EBL family. FIG. 3 shows these regions and the consensus amino acid sequences derived from them.

A. General Methods

Much of the nomenclature and general laboratory procedures required in this application can be found in Sambrook, et al., Molecular Cloning *A Laboratory Manual* (2nd Ed.), Vol. 1–3, Cold Spring Harbor Laboratory, Cold Spring Harbor, N.Y., 1989. The manual is hereinafter referred to as "Sambrook, et al."

B. Methods for Isolating DNA Encoding SABP, DABP and EBL Binding Regions

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the binding domains of the invention, such as subcloning nucleic acid sequences encoding polypeptides into expression vectors, labelling probes, DNA hybridization, and the like are described generally in Sambrook et al., incorporated herein by reference.

Recombinant DNA techniques can be used to produce the binding domain polypeptides. In general, the DNA encoding the SABP and DABP binding domains are first cloned or isolated in a form suitable for ligation into an expression vector. After ligation, the vectors containing the DNA fragments or inserts are introduced into a suitable host cell for expression of the recombinant binding domains. The polypeptides are then isolated from the host cells.

There are various methods of isolating the DNA sequences encoding the SABP, DABP and EBL binding domains. Typically, the DNA is isolated from a genomic or cDNA library using labelled oligonucleotide probes specific for sequences in the DNA. Restriction endonuclease digestion of genomic DNA or cDNA containing the appropriate genes can be used to isolate the DNA encoding the binding domains of these proteins. Since the DNA sequences of the SABP and DABP genes are known, a panel of restriction endonucleases can be constructed to give cleavage of the DNA in the desired regions. After restriction endonuclease digestion, DNA encoding SABP binding domain or DABP binding domain is identified by its ability to hybridize with nucleic acid probes, for example on Southern blots, and these DNA regions are isolated by standard methods familiar to those of skill in the art. See Sambrook, et al.

The polymerase chain reaction can also be used to prepare DABP, SABP EBL binding domain DNA. Polymerase chain reaction technology (PCR) is used to amplify nucleic acid sequences of the DABP and SABP binding domains directly from mRNA, from cDNA, and from genomic libraries or cDNA libraries. The primers shown in FIG. 3 are particularly preferred for this process.

Appropriate primers and probes for amplifying the SABP and DABP binding region DNA's are generated from analysis of the DNA sequences. In brief, oligonucleotide primers complementary to the two 3' borders of the DNA region to be amplified are synthesized. The polymerase chain reaction is then carried out using the two primers. See *PCR Protocols: A Guide to Methods and Applications.* (Innis, M, Gelfand, D., Sninsky, J. and White, T., eds.), Academic Press, San Diego (1990). Primers can be selected to amplify the entire DABP regions or to amplify smaller segments of the DABP and SABP binding domains, as desired.

Oligonucleotides for use as probes are chemically synthesized according to the solid phase phosphoramidite triester method first described by Beaucage, S. L. and Caruthers, M. H., 1981, Tetrahedron Letts., 22(20):1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The sequence of the synthetic oligonucleotides can be verified using the chemical degradation method of Maxam, A. M. and Gilbert, 1980, in W., Grossman, L. and Moldave, D., eds. Academic Press, New York, Methods in Enzymology, 65:499–560.

Other methods known to those of skill in the art may also be used to isolate DNA encoding all or part of the SABP or DABP binding domains. See Sambrook, et al.

C. Expression of DABP, SABP and EBL Binding Domain Polypeptides

Once the binding domain DNAs are isolated and cloned, one may express the desired polypeptides in a recombinantly engineered cell such as bacteria, yeast, insect (especially employing baculoviral vectors), and mammalian cells. It is expected that those of skill in the art are knowledgeable in the numerous expression systems available for expression of the DNA encoding the DABP and SABP binding domains. No attempt to describe in detail the various methods known for the expression of proteins in prokaryotes or eukaryotes will be made.

In brief summary, the expression of natural or synthetic nucleic acids encoding binding domains will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the binding domains. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, C., 1984, J. Bacteriol., 158:1018–1024 and the leftward promoter of phage lambda ($P_L$) as described by Herskowitz, I. and Hagen, D., 1980, Ann. Rev. Genet., 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the DABP and SABP binding domains are available using *E. coli, Bacillus* sp. (Palva, I et al., 1983, Gene 22:229–235; Mosbach, K. et al. Nature, 302:543–545)and *Salmonella. E. coli* systems are preferred.

The binding domain polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of the expressed antigen is achieved by methods known in the art as radioimmunoassays, Western blotting techniques or immunoprecipitation. Purification from *E. coli* can be achieved following procedures described in U.S. Pat. No. 4,511,503.

2. Synthesis of SABP, DABP and EBL Binding Domains in Eukaryotes

A variety of eukaryotic expression systems such as yeast, insect cell lines and mammalian cells, are known to those of skill in the art. As explained briefly below, the DABP and SABP binding domains may also be expressed in these eukaryotic systems.

a. Expression in Yeast

Synthesis of heterologous proteins in yeast is well known and described. *Methods in Yeast Genetics*, Sherman, F., et al., Cold Spring Harbor Laboratory, (1982) is a well recognized work describing the various methods available to produce the binding domains in yeast.

Examples of promoters for use in yeast include GAL1,10 (Johnson, M., and Davies, R. W., 1984, Mol. and Cell. Biol., 4:1440–1448) ADH2 (Russell, D., et al. 1983, J. Biol. Chem., 258:2674–2682), PH05 (EMBO J. 6:675–680, 1982), and MFα1 (Herskowitz, I. and Oshima, Y., 1982, in The Molecular Biology of the Yeast Saccharomyces, (eds. Strathern, J. N. Jones, E. W., and Broach, J. R., Cold Spring Harbor. Lab., Cold Spring Harbor, N.Y., pp. 181–209. A multicopy plasmid with a selective-marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17–24; Broach, et al., 1979, Gene, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104–109; and Hinnen, A., et al., 1978, Proc. Natl. Acad. Sci. USA, 75:1929–1933. The second procedure does not involve removal of the cell wall. Instead the cells are treated with lithium chloride or acetate and PEG and put on selective plates (Ito, H., et al., 1983, J. Bact., 153:163–168).

The binding domains can be isolated from yeast by lysing the cells and applying standard protein isolation techniques to the lysates. The monitoring of the purification process can be accomplished by using Western blot techniques or radio-immunoassays of other standard immunoassay techniques.

b. Expression in Mammalian and Insect Cell Cultures

Illustrative of cell cultures useful for the production of the binding domains are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e. g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are obtained from the SV-40 promoter (Science, 222:524–527, 1983), the CMV I.E. Promoter (Proc. Natl. Acad. Sci. 81:659–663, 1984) or the metallothionein promoter (Nature 296:39–42, 1982). The cloning vector containing the expression control sequences is cleaved using restriction enzymes and adjusted in size as necessary or desirable and ligated with DNA coding for the SABP or DABP polypeptides by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, J. Virol. 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach. Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed DABP and SABP binding domain polypeptides are isolated from cells grown as suspensions or as monolayers. The latter are recovered by well known mechanical, chemical or enzymatic means.

c. Expression in Recombinant Vaccinia Virus- or Adenovirus-infected Cells

In addition to use in recombinant expression systems, the isolated binding domain DNA sequences can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the DABP and SABP binding domain polypeptides into plasmids so that they are flanked by viral sequences on both sides. The DNA's encoding the binding domains are then inserted into the virus genome through homologous recombination.

A recombinant adenovirus can be produced, for example, by ligating together two plasmids each containing about 50% of the viral sequence and the DNA sequence encoding erythrocyte binding domain polypeptide. Recombinant RNA viruses such as the alpha virus can be made via a CDNA intermediate using methods known in the art.

In the case of vaccinia virus (for example, strain WR), the DNA sequence encoding the binding domains can be inserted in the genome by a number of methods including homologous recombination using a transfer vector, pTKgpt-OFIS as described in Kaslow, et al., *Science* 252:1310–1313 (1991), which is incorporated herein by reference.

Alternately the DNA encoding the SABP and DABP binding domains may be inserted into another plasmid designed for producing recombinant vaccinia, such as pGS62, Langford, C. L., et al., 1986, *Mol. Cell. Biol.* 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using CDNA encoding the DABP and SABP binding domain polypeptides and by immunodetection techniques using antibodies specific for the expressed binding domain polypeptides. Virus stocks may be prepared by infection of cells such as HELA S3 spinner cells and harvesting of virus progeny.

The recombinant virus of the present invention can be used to induce anti-SABP and anti-DABP binding domain antibodies in mammals, such as mice or humans. In addition, the recombinant virus can be used to produce the SABP and DABP binding domains by infecting host cells in vitro, which in turn express the polypeptide (see section on expression of SABP and DABP binding domains in eukaryotic cells, above).

The present invention also relates to host cells infected with the recombinant virus. The host cells of the present invention are preferably mammalian, such as BSC-1 cells. Host cells infected with the recombinant virus express the DABP and SABP binding domains on their cell surfaces. In addition, membrane extracts of the infected cells induce protective antibodies when used to inoculate or boost previously inoculated mammals.

D. Purification of the SABP, DABP and EBL Binding Domain Polypeptides

The binding domain polypeptides produced by recombinant DNA technology may be purified by standard techniques well known to those of skill in the art. Recombinantly produced binding domain polypeptides can be directly expressed or expressed as a fusion protein. The protein is then purified by a combination of cell lysis (e. g., sonication) and affinity chromatography. For fusion products, subsequent digestion of the fusion protein with an appropriate proteolytic enzyme release the desired SABP and DABP binding domains.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

E. Production of Binding Domains by Protein Chemistry Techniques

The polypeptides of the invention can be synthetically prepared in a wide variety of ways. For instance polypeptides of relatively short size, can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984).

Alternatively, purified and isolated SABP, DABP or EBL family proteins may be treated with proteolytic enzymes in order to produce the binding domain polypeptides. For example, recombinant DABP and SABP proteins may be used for this purpose. The DABP and SABP protein sequence may then be analyzed to select proteolytic enzymes to be used to generate polypeptides containing desired regions of the DABP and SABP binding domain. The desired polypeptides are then purified by using standard techniques for protein and peptide purification, For a review of standard techniques see, *Methods in Enzymology*, "Guide to Protein Purification", M. Deutscher, ed. Vol. 182 (1990), pages 619–626, which is incorporated herein by reference.

F. Modification of Nucleic Acid and Polypeptide Sequences

The nucleotide sequences used to transfect the host cells used for production of recombinant binding domain polypeptides can be modified according to standard techniques to yield binding domain polypeptides, with a variety of desired properties. The binding domain polypeptides of the present invention can be readily designed and manufactured utilizing various recombinant DNA techniques well known to those skilled in the art. For example, the binding domain polypeptides can vary from the naturally-occurring sequence at the primary structure level by amino acid insertions, substitutions, deletions, and the like. These modifications can be used in a number of combinations to produce the final modified protein chain.

The amino acid sequence variants can be prepared with various objectives in mind, including facilitating purification and preparation of the recombinant polypeptides. The modified polypeptides are also useful for modifying plasma half-life, improving therapeutic efficacy, and lessening the severity or occurrence of side effects during therapeutic use. The amino acid sequence variants are usually predetermined variants not found in nature but exhibit the same immunogenic activity as naturally occurring polypeptides. For instance, polypeptide fragments comprising only a portion (usually at least about 60–80%, typically 90–95%) of the primary structure may be produced. For use as vaccines, polypeptide fragments are typically preferred so long as at least one epitope capable of eliciting production of blocking antibodies remains.

In general, modifications of the sequences encoding the binding domain polypeptides may be readily accomplished by a variety of well-known techniques, such as site-directed mutagenesis (see, Giliman and Smith, *Gene* 8:81–97 (1979) and Roberts, S. et al., *Nature* 328:731–734 (1987)). One of ordinary skill will appreciate that the effect of many mutations is difficult to predict. Thus, most modifications are evaluated by routine screening in a suitable assay for the desired characteristic. For instance, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

G. Diagnostic and Screening Assays

The polypeptides of the invention can be used in diagnostic applications for the detection of merozoites in a biological sample. The presence of parasites can be detected using several well recognized specific binding assays based on immunological results. (See U.S. Pat. Nos. 4,366,241; 4,376,110; 4,517,288; and 4,837,168, which are hereby incorporated by reference.) For instance, labeled monoclonal antibodies to polypeptides of the invention can be used to detect merozoites in a biological sample. Alternatively, labelled polypeptides of the invention can be used to detect the presence of antibodies to SABP or DABP in a biological sample. For a review of the general procedures in diagnostic immunoassays, see also *Basic and Clinical Immunology* 7th Edition (D. Stites and A. Terr ed.) 1991, which is hereby incorporated by reference.

In addition, modified polypeptides, antibodies or other compounds capable of inhibiting the interaction between SABP or DABP and erythrocytes can be assayed for biological activity. For instance, polypeptides can be recombinantly expressed on the surface of cells and the ability of the cells to bind erythrocytes can be measured as described below. Alternatively, peptides or antibodies can tested for the ability to inhibit binding between erythrocytes and merozoites or SABP and DABP.

Cell-free assays can also be used to measure binding of DABP or SABP polypeptides to isolated Duffy antigen or glycophorin polypeptides. For instance, the erythrocyte proteins can be immobilized on a solid surface and binding of labelled SABP or DABP polypeptides can be measured.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^{3}H$, $^{125}I$, $^{35}S$, $^{14}C$, or $^{32}P$ labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

In addition, the polypeptides of the invention can be assayed using animal models, well known to those of skill in the art. For *P. falciparum* the in vivo models include *Aotus* sp. monkeys or chimpanzees; for *P. vivax* the in vivo models include *Saimiri* monkeys.

H. Pharmaceutical Compositions Comprising Binding Domain Polypeptides

The polypeptides of the invention are useful in therapeutic and prophylactic applications for the treatment of malaria. Pharmaceutical compositions of the invention are suitable for use in a variety of drug delivery systems. Suitable formulations for use in the present invention are found in *Remington's Pharmaceutical Sciences*, Mack Publishing company, Philadelphia, Pa., 17th ed. (1985), which is incorporated herein by reference. For a brief review of methods for drug delivery, see, Langer, *Science* 249: 1527–1533 (1990), which is incorporated herein by reference.

The polypeptides of the present invention can be used in pharmaceutical and vaccine compositions that are useful for administration to mammals, particularly humans. The polypeptides can be administered together in certain circumstances, e.g. where infection by both *P. falciparum* and *P. vivax* is likely. Thus, a single pharmaceutical composition can be used for the treatment or prophylaxis of malaria caused by both parasites.

The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate; and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In certain embodiments patients with malaria may be treated with SABP or DABP polypeptides or other specific blocking agents (e.g. monoclonal antibodies) that prevent binding of *Plasmodium* merozoites and schizonts to the erythrocyte surface.

The amount administered to the patient will vary depending upon what is being administered, the state of the patient and the manner of administration. In therapeutic applications, compositions are administered to a patient already suffering from malaria in an amount sufficient to inhibit spread of the parasite through erythrocytes and thus cure or at least partially arrest the symptoms of the disease and its complications. An amount adequate to accomplish this is defined as "therapeutically effective dose." Amounts effective for this use will depend on the severity of the disease and the weight and general state of the patient. But will generally be in the range of about 1 mg to about 5 gm per day, preferably about 100 mg per day, for a 70 kg patient.

Alternatively, the polypeptides of the invention can be used prophylactically as vaccines. The vaccines of the invention contain as an active ingredient an immunogenically effective amount of the binding domain polypeptide or of a recombinant virus as described herein. The immune response may include the generation of antibodies; activation of cytotoxic T lymphocytes (CTL) against cells presenting peptides derived from the peptides encoded by the SABP, DABP or EBL sequences of the present invention, or other mechanisms well known in the art. See e.g. Paul *Fundamental Immunology Second Edition* published by Raven press New York (incorporated herein by reference) for a description of immune response. Useful carriers are well known in the art, and include, for example, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

The DNA or RNA encoding the SABP or DABP binding domains and the EBL gene family motifs may be introduced into patients to obtain an immune response to the polypeptides which the nucleic acid encodes. Wolff et. al., *Science* 247: 1465–1468 (1990) which is incorporated herein by reference describes the use of nucleic acids to produce expression of the genes which the nucleic acids encode.

Vaccine compositions containing the polypeptides, nucleic acids or viruses of the invention are administered to a patient to elicit a protective immune response against the polypeptide. A "protective immune response" is one which prevents or inhibits the spread of the parasite through erythrocytes and thus at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 µg to about 1 gm of peptide for a 70 kg patient, followed by boosting dosages of from about 100 µg to about 1 gm of the polypeptide pursuant to a boosting regimen over weeks to months depending upon the patient's response and condition e.g. by measuring levels of parasite in the patient's blood. For nucleic acids, typically 30–100 ug of nucleic acid is injected into a 70 kg patient, more typically about 50–150 ug of nucleic acid is injected into a 70 kg patient followed by boosting doses as appropriate.

The following example is offered by way of illustration, not by way of limitation.

EXAMPLE

Identification of the Amino-terminal, Cysteine-rich Region of SABP and DABP as Binding Domains for Erythrocytes 1. Expression of the SABP Binding Domain Polypeptide on the Surface of Cos cells.

To demonstrate that the amino-terminal, cysteine-rich region of the SABP protein is the sialic acid binding region, this region of the protein was expressed on the surface of mammalian Cos cells in vitro. This DNA sequence is from position 1 to position 1848 of the SABP DNA sequence (SEQ ID No 3). Polymerase chain reaction technology (PCR) was used to amplify this region of the SABP DNA directly from the cloned gene.

Sequences corresponding to restriction endonuclease sites for Pvull or Apal were incorporated into the oligonucleotide sequence of the probes used in PCR amplification in order to facilitate insertion of the PCR-amplified regions into the pRE4 vector (see below). The specific oligonucleotides, (SEQ ID NO:34) 5'-ATCGATCAGCTGGGAAGAAATA-CTTCATCT-3' and (SEQ ID NO:35) 5'-ATCGATGGGCC-CCGAAGTTTGTTCATTATT-3' were synthesized. These oligonucleotides were used as primers to PCR-amplify the region of the DNA sequence encoding the cysteine-rich amino terminal region of the SABP protein.

PCR conditions were based on the standard described in Saiki, et al., Science 239: 487–491 (1988). Template DNA was provided from cloned fragments of the gene encoding SABP which had been spliced and re-cloned as a single open-reading frame piece.

The vector, pRE4, used for expression in Cos cells is shown in FIG. 1. The vector has an SV40 origin of replication, an ampicillin resistance marker and the Herpes simplex virus glycoprotein D gene (HSV glyd) cloned downstream of the Rous sarcoma virus long terminal repeats (RSV LTR). Part of the extracellular domain of the HSV glyd gene was excised using the Pvull and Apal sites in HSV glyd.

As described above, the PCR oligonucleotide primers contained the Pvull or Apal restriction sites. The PCR-amplified DNA fragments obtained above were digested with the restriction enzymes Pvull and Apal and cloned into the Pvull and Apal sites of the vector pRE4. These constructs were designed to express regions of the SABP protein as chimeric proteins with the signal sequence of HSV glyd at the N-terminal end and the transmembrane and cytoplasmic domain of HSV glyd at the C-terminal end. The signal sequence of HSV glyd targets these chimeric proteins to the surface of Cos cells and the transmembrane segment of HSV glyd anchors these chimeric proteins to the Cos cell surface.

Mammalian Cos cells were transfected with the pRE4 constructs containing the PCR-amplified SABP DNA regions, by calcium phosphate precipitation according to standard techniques.

2. Expression of the DABP Binding Domain Polypeptide on the Surface of Cos cells.

To demonstrate that the amino-terminal, cysteine-rich region of the DABP protein is the binding domain, this region was expressed on the surface of Cos cells. This region of the DNA sequence from position 1–975 was first PCR-amplified (SEQ ID No 1).

Sequences corresponding to restriction endonuclease sites for Pvull or Apal were incorporated into the oligonucleotide probes used for PCR amplification in order to facilitate subsequent insertion of the amplified DNA into the pRE4 vector, as described above. The oligonucleotides (SEQ ID NO:36) 5'-TCTCGTCAGCTGACGATCTCTAGTGCTA-TT-3' and (SEQ ID NO:37) 5'-ACGAGTGGGCCCTGT-CACAACTTCCTGAGT-3' were synthesized. These oligonucleotides were used as primers to amplify the region of the DABP DNA sequence encoding the cysteine-rich, amino-terminal region of the DABP protein directly from the cloned DABP gene, using the same conditions described above.

The same pRE4 vector described above in the section on expression of SABP regions in Cos cells was also used as a vector for the DABP DNA regions.

3. Binding Studies with Erythrocytes.

To demonstrate their ability to bind human erythrocytes, the transfected Cos cells expressing binding domains from DABP and SABP were incubated with erythrocytes for two hours at 37° C. in culture media (DMEM/10% FBS). The non-adherent erythrocytes were removed with five washes of phosphate-buffered saline and the bound erythrocytes were observed by light microscopy. Cos cells expressing the amino terminal, cysteine-rich SABP polypeptides on their surface bound untreated human erythrocytes, but did not bind neuraminidase treated erythrocytes, that is, erythrocytes which lack sialic acid residues on their surface (data not shown). Cos cells expressing other regions of the SABP protein on their surface did not bind human erythrocytes (data not shown). These results identified the amino-terminal, cysteine-rich region of SABP as the erythrocyte binding domain and indicated that the binding of Cos cells expressing these regions to human erythrocytes is specific. Furthermore, the binding of the expressed region to erythrocytes is identical to the binding pattern seen for the authentic SABP-175 molecule upon binding to erythrocytes.

Similarly, Cos cells expressing the amino-terminal cysteine-rich region of DABP on their surface bound Duffy-positive human erythrocytes, but did not bind Duffy-negative human erythrocytes, that is erythrocytes which lack the Duffy blood group antigen (data not shown). Cos cells expressing other regions of the DABP protein on their surface did not bind human erythrocytes (data not shown). These results identified the amino-terminal cysteine rich region of DABP as the erythrocyte binding domain and indicated that the binding of the Cos cells was specific.

What is claimed is:

1. An isolated polynucleotide sequence encoding an erythrocyte binding antigen comprising the cysteine-rich domain of EBL-e1 (SEQ ID NO: 16).

\* \* \* \* \*